US008999658B2

(12) United States Patent
Gozal et al.

(10) Patent No.: US 8,999,658 B2
(45) Date of Patent: Apr. 7, 2015

(54) METHODS AND KITS FOR DIAGNOSING OBSTRUCTIVE SLEEP APNEA

(75) Inventors: David Gozal, Chicago, IL (US); Saeed A. Jortani, Louisville, KY (US); Roland Valdes, Jr., Simpsonville, KY (US); Leila Kheirandish-Gozal, Chicago, IL (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 225 days.

(21) Appl. No.: 13/121,037

(22) PCT Filed: Sep. 25, 2009

(86) PCT No.: PCT/US2009/058392
§ 371 (c)(1),
(2), (4) Date: May 20, 2011

(87) PCT Pub. No.: WO2010/036901
PCT Pub. Date: Apr. 1, 2010

(65) Prior Publication Data
US 2011/0217719 A1    Sep. 8, 2011

Related U.S. Application Data

(60) Provisional application No. 61/242,640, filed on Sep. 15, 2009, provisional application No. 61/100,517, filed on Sep. 26, 2008.

(51) Int. Cl.
G01N 33/68    (2006.01)
G01N 33/573   (2006.01)
C12Q 1/37     (2006.01)
H01J 49/26    (2006.01)

(52) U.S. Cl.
CPC .... G01N 33/6896 (2013.01); G01N 2800/2864 (2013.01)

(58) Field of Classification Search
None
See application file for complete search history.

(56) References Cited

U.S. PATENT DOCUMENTS 7,815,905 B2 *   10/2010   Chen et al. .................. 424/130.1
2006/0029980 A1   2/2006   Gozal et al.
2006/0293232 A1  12/2006   Levy et al.
2007/0269836 A1 * 11/2007   McPherson et al. ........... 435/7.4

OTHER PUBLICATIONS

Pepels et al. Placental urocortin-2 and -3: endocrine or paracrine functioning during healthy pregnancy? Placenta. Jun. 2010;31(6):475-81. Epub May 6, 2010.*
Takahashi et al. Expression of urocortin III/stresscopin in human heart and kidney. J Clin Endocrinol Metab. Apr. 2004;89(4):1897-903.*
Yata et al. Suppression of progesterone production by stresscopin/urocortin 3 in cultured human granulosa-lutein cells. Hum Reprod. Jul. 2009;24(7):1748-53. Epub Apr. 7, 2009.*
Amin et al., "Activity-adjusted 24-hour ambulatory blood pressure and cardiac remodeling in children with sleep disordered breathing," Hypertension, 2008, vol. 51(1), pp. 84-91.
Andersen et al., "The antiheparin effect of α1-acid glycoprotein probably due to steric hindrance of the heparin-thrombin interaction," Thromb. Res., 1979, vol. 15, pp. 857-868.
Bell et al., "The RNA binding protein Zfp361l is required for normal vascularisation and post-transcriptionally regulates VEGF expression," Dev Dyn, 2006, vol. 235(11), pp. 3144-3155.
Benedek et al., "Serum protein binding and the role of increased alpha 1-acid glycoprotein in moderately obese male subjects," Br J Clin Pharmacol, 1984, vol. 18, pp. 941-946.
Bhattacharjee et al., "Nocturnal polysomnographic characteristics of habitually snoring children initially referred to pediatric ENT or sleep clinics," Sleep Med, 2009, vol. 10, pp. 1031-1034.
Bhattacharjee et al., "Cardiovascular complications of obstructive sleep apnea syndrome: evidence from children," Prog Cardiovasc Dis, 2009, vol. 51(5), pp. 416-433.
Boncela et al., "Acute phase protein α1-acid glycoprotein interacts with plasminogen activator inhibitor type 1 and stabilizes its inhibitory activity," J. Biol. Chem., 2001, vol. 276, pp. 35305-35311.
Carroll et al., "Inability of clinical history to distinguish primary snoring from obstructive sleep apnea syndrome in children," Chest, 1995, vol. 108(3), pp. 610-618.
Chen et al., "Renal kallikrein in chronic hypoxic rats," Clin Exp Pharmacol Physiol, 1996, vol. 23(9), pp. 819-824.
Christiansen et al., "Increased urinary orosomucoid excretion: a proposed marker for inflammation and endothelial dysfunction in patients with type 2 diabetes," Scand J Clin Lab Invest, 2009, vol. 69(2), pp. 272-281.
Christiansen et al., "Particle-enhanced turbidimetric immunoassay for quantitative determination of orosomucoid in urine: development, validation and reference values," Clin Chem Lab Med, 2004, vol. 42, pp. 1168-1177.
Costello et al., "Inhibition of neutrophil activation by α1-acid glycoprotein,"Clin. Exp. Immunol., 1984, vol. 55, pp. 465-472.
De Graaf et al., "Inflammation-induced expression of sialyl LewisX-containing glycan structures on α1-acid glycoprotein (orosomucoid) in human sera," J. Exp. Med., 1993, vol. 177, pp. 657-666.
Deng et al., "Human tribbles homologue 2 is expressed in unstable regions of carotid plaques and regulates macrophage IL-10 in vitro," Clin Sci (Lond), 2009, vol. 116(3), pp. 241-248.

(Continued)

*Primary Examiner* — David Romeo
(74) *Attorney, Agent, or Firm* — Stites & Harbison PLLC; Terry L. Wright

(57) ABSTRACT

The presently-disclosed subject matter provides methods and kits for diagnosing obstructive sleep apnea (OSA) in a subject, such as a human child, wherein a biological sample is provided from the subject and the amount of a Urocortin III peptide is determined from the sample. Further provided are methods for diagnosing OSA in a subject wherein the amount of a Urocortin III peptide and one or more peptides selected from a Uromodulin peptide, an Orosomucoid 1 peptide, and a Kallikrein 1 peptide are determined in a biological sample from a subject.

13 Claims, 5 Drawing Sheets

(56) References Cited

OTHER PUBLICATIONS

"EEG arousals: scoring rules and examples: a preliminary report from the Sleep Disorders Atlas Task Force of the American Sleep Disorders Association," Sleep, 1992, vol. 15(2), pp. 173-184.

El-Achkar et al., "Tamm-Horsfall protein protects the kidney from ischemic injury by decreasing inflammation and altering TLR4 expression." Am J Physiol Renal Physiol, 2008, vol. 295(2), pp. F534-F544.

Ferreira et al., "Snoring in Portuguese primary school children," Pediatrics, 2000, vol. 106(5), pp. 1128-1129.

Fournier et al., "Alpha-1-acid glycoprotein." Biochim Biophys Acta, 2000, vol. 1482(1-2), pp. 157-171.

Fukuoka et al., "Analysis of the C-terminal structure of urinary Tamm—Horsfall protein reveals that the release of the glycosyl phosphatidylinositol-anchored counterpart from the kidney occurs by phenylalanine-specific proteolysis," Biochem Biophys Res Commun, 2001, vol. 289, pp. 1044-1048.

Ginouves et al., "PHDs overactivation during chronic hypoxia "desensitizes" HIFalpha and protects cells from necrosis," Proc Natl Acad Sci U S A, 2008, vol. 105(12), pp. 4745-4750.

Gozal, D., "Obstructive sleep apnea in children: implications for the developing central nervous system," Semin Pediatr Neurol, Jun. 2008, vol. 15(2), pp. 100-106.

Gozal et al., "Metabolic alterations and systemic inflammation in obstructive sleep apnea among nonobese and obese prepubertal children," Am J Respir Crit Care Med, 2008, vol. 177(10), pp. 1142-1149.

Gozal et al., "Cardiovascular morbidity in obstructive sleep apnea: oxidative stress, inflammation, and much more," Am J Respir Crit Care Med, 2008, vol. 177(4): pp. 369-375.

Gozal et al., "Systemic inflammation in non-obese children with obstructive sleep apnea," Sleep Med, 2008, vol. 9(3), pp. 254-259.

Gozal et al., "Obstructive sleep apnea and endothelial function in school-aged nonobese children: effect of adenotonsillectomy," Circulation, 2007, vol. 116(20), pp. 2307-2314.

Gozal et al., "Circulating vascular endothelial growth factor levels in patients with obstructive sleep apnea," Sleep, 2001, vol. 25(1), pp. 59-65.

Guder et al., "Clinical role of urinary low molecular weight proteins: their diagnostic and prognostic implications," Scand J Clin Lab Invest Supplm, 2008, vol. 241, pp. 95-98.

Jiang et al., "Increased urinary excretion of orosomucoid is a risk predictor of diabetic nephropathy," Nephrology, 2009 vol. 14, pp. 332-337.

Kaditis et al., "Sleep-disordered breathing in 3,680 Greek children," Pediatr Pulmonol, 2004, vol. 37, pp. 499-509.

Khalyfa et al., "Genome-wide gene expression profiling in children with non-obese obstructive sleep apnea," Sleep Med, 2009, vol. 10(1), pp. 75-86.

Krishna et al., "Urinary protein expression patterns in children with sleep-disordered breathing: preliminary findings," Sleep Med, 2006, vol. 7(3), pp. 221-227.

Kwon et al., "Suppression of vascular endothelial growth factor expression at the transcriptional and post-transcriptional levels," Nucleic Acids Res, 2005, vol. 33(8), e74.

Larbi et al., "2D-DIGE: Comparative proteomics of cellular signaling pathways," Methods Mol Biol, 2009, vol. 517, pp. 1-28.

Lavie et al., "Plasma vascular endothelial growth factor in sleep apnea syndrome: effects of nasal continuous positive air pressure treatment.," Am J Respir Crit Care Med, 2002, vol. 165(12), pp. 1624-1628.

Liu et al., "A model for random sampling and estimation of relative protein abundance in shotgun proteomics," Anal Chem, 2004, vol. 76, pp. 4193-4201.

Lynn et al., "Excretion of Tamm—Horsfall glycoprotein in renal disease," Clin Nephrol, 1984, vol. 22, pp. 253-257.

MacKiewicz et al., "Monokines regulate glycosylation of acute-phase proteins," J. Exp. Med., 1987, vol. 166, pp. 253-258.

Maachi et al., "Systemic low-grade inflammation is related to both circulating and adipose tissue TNFalpha, leptin and IL-6 levels in obese women," Int J Obes Relat Metab Disord, 2004, vol. 28(8), pp. 993-997.

Montgomery-Downs et al., "Polysomnographic characteristics in normal preschool and early school-aged children," Pediatrics, 2006, vol. 117(3), pp. 741-753.

Montgomery-Downs et al., "Sleep habits and risk factors for sleep-disordered breathing in infants and young toddlers in Louisville, Kentucky," Sleep Med, 2006, vol. 7, pp. 211-219.

Montgomery-Downs et al., "Snoring and sleep-disordered breathing in young children: Subjective and objective correlates," 2004, Sleep, vol. 27, pp. 87-94.

Naiki et al., "TRB2, a mouse Tribbles ortholog, suppresses adipocyte differentiation by inhibiting AKT and C/EBPbeta," J Biol Chem, 2007, vol. 282(33), pp. 24075-24082.

Nesvizhskii et al., "Analysis and validation of proteomic data generated by tandem mass spectrometry," Nat Methods, 2007, vol. 4, pp. 787-797.

O'Brien et al., "Neurobehavioral correlates of sleep-disordered breathing in children," J Sleep Res, Jun. 13, 2004(2), pp. 165-172.

O'Brien et al., "Sleep and neurobehavioral characteristics in 5-7-year-old hyperactive children," Pediatrics, 2003, vol. 111, pp. 554-563.

"Obstructive Sleep Apnea Syndrome. Technical report: diagnosis and management of childhood obstructive sleep apnea syndrome," Pediatrics, 2002, vol. 109(4), e69.

Old et al., "Comparison of label-free methods for quantifying human proteins by shotgun proteomics," Mol Cell Proteomics, 2005, vol. 4, pp. 1487-1502.

Penders et al., "Alpha 1-microglobulin: clinical laboratory aspects and applications," Clin Chim Acta, 2004, vol. 346 (2), pp. 107-118.

Pisitkun et al., "Identification and proteomic profiling of exosomes in human urine," Proc Natl Acad Sci U S A, 2004, vol. 101, pp. 13368-13373.

Pugia et al., "Bikunin (urinary trypsin inhibitor): structure, biological relevance, and measurement," Adv Clin Chem, 2007, vol. 44, pp. 223-245.

Pugia et al., "Immunological evaluation of urinary trypsin inhibitors in blood and urine: role of N- & O-linked glycoproteins,." Glycoconj J, 2007, vol. 24(1), pp. 5-15.

Raynaud-Simon et al., "Orosomucoid: a mortality risk factor in elderly people living in the community?," Clin Nutr, 2002, vol. 21(1), pp. 45-50.

Reiner et al., "Identifying differentially expressed genes using false discovery rate controlling procedures," Bioinformatics, 2003, vol. 19, pp. 368-375.

Rosen et al., "Prevalence and risk factors for sleep-disordered breathing in 8- to 11-year-old children: association with race and prematurity," J Pediatr, 2003, vol. 142, pp. 383-389.

Capdevila et al., "Pediatric obstructive sleep apnea: Complications, management, and long-term outcomes," Proc Am Thor Soc, 2008, vol. 5, pp. 274-282.

Schmid et al., "The carbohydrate units of human plasma α1-acid glycoprotein," Biochim. Biophys. Acta., 1977, vol. 492, pp. 291-302.

Setafini-Cessi et al., "Tamm—Horsfall glycoprotein: biology and clinical relevance," Am J Kidney Dis, 2003, vol. 42, pp. 658-676.

Slominski et al., "The skin produces urocortin," Journal of Clinical Endocrinology & Metabolism, Feb. 2000, vol. 85(2), pp. 815-823.

Sorensson et al., "Human endothelial cells produce orosomucoid, an important component of the capillary barrier," Am. J. Physiol, 1999, vol. 276, pp. H530-H534.

Thongboonkerd et al., "Proteomic analysis reveals alterations in the renal kallikrein pathway during hypoxia-induced hypertension," J Biol Chem. 277,2002, vol. (38), pp. 34708-34716.

Thornley et al., "Human Tamm—Horsfall glycoprotein: urinary and plasma levels in normal subjects and patients with renal disease determined by a fully validated radioimmunoassay," Clin Sci (Lond), 1985, vol. 68, pp. 529-535.

(56) References Cited

OTHER PUBLICATIONS

Zolotarjova et al., "Differences among techniques for high-abundant protein depletion," Proteomics, 2005, vol. 5, pp. 3304-3313.

ISA/US, International Search Report and Written Opinion for corresponding International Application No. PCT/US09/58392, completed Nov. 5, 2009.

Gozal et al., "2D-DIGE Proteomic Approaches Reveal Urine Candidate Biomarkers in Pediatric Obstructive Sleep Apnea," Am. J. Respir. Crit. Care Med., Sep. 24, 2009 (abstract available at http://ajrccm.atsajournals.org/cgi/content/abstract/200905-0765OCv1).

Lewis et al., "Identification of urocortin III, an additional member of the corticotropin-releasing factor (CRF) family with high affinity for the CRF2 receptor," PNAS, 2001, vol. 1(13), pp. 7570-7575.

* cited by examiner

Tenascin

Tribbles homologue 2

Zinc finger protein 81

METHODS AND KITS FOR DIAGNOSING OBSTRUCTIVE SLEEP APNEA

RELATED APPLICATIONS

This application claims priority to U.S. Provisional Application Ser. No. 61/100,517, filed Sep. 26, 2008, and U.S. Provisional Application Ser. No. 61/242,640, filed Sep. 15, 2009, the entire disclosures of which are incorporated herein by this reference.

GOVERNMENT INTEREST

This invention was made with government support under Grant Numbers DK072923, HL065270, and HL086662 awarded by the National Institutes of Health. The government has certain rights in the invention.

TECHNICAL FIELD

The presently-disclosed subject matter relates to methods of diagnosing obstructive sleep apnea (OSA) and distinguishing OSA from primary snoring (PS). In particular, the presently-disclosed subject matter relates to diagnostic and prognostic methods that make use of biomarkers for OSA.

BACKGROUND

Obstructive Sleep Apnea (OSA) is a frequent condition affecting up to 3% of all pre-pubertal children and has now been recognized as imposing substantial physiological, neurological, and cognitive consequences (1-3). Indeed, if left untreated, OSA can lead to serious neurobehavioral and cardiovascular consequences. Among the first, daytime sleepiness, irritability, depression, attention deficit hyperactivity disorder (ADHD)-like behaviors, and poor cognitive function have all been reported in children suffering from OSA. In this regard, it has also been reported that OSA in children strongly and dose-dependently correlates with emotional problems, impaired school performance, hyperactivity, and aggressive and withdrawal behaviors. With respect to the cardiovascular consequences, untreated OSA been linked to hypertension, increased risk of myocardial infarction, and stroke. Furthermore, severe and longstanding cases of OSA have been associated with pulmonary hypertension and, in some cases, sudden unexpected death. Despite the seriousness of these consequences of OSA, however, it has been shown that some of these adverse consequences can be reversed if the OSA is diagnosed and treated early.

In the clinical setting, history and physical examination have extremely poor predictive value in differentiating between primary snoring (PS) and OSA (12-15). As such, current diagnostic approaches for OSA require an overnight sleep study or polysomnography (PSG) in a sleep laboratory, which is both costly and inconvenient, as well as labor intensive. Furthermore, due to the relative unavailability of suitable sleep facilities, particularly, pediatric sleep facilities, long waiting periods and unnecessary delays in diagnosis and treatment are frequent. Accordingly, the development of non-invasive biomarkers capable of reliably distinguishing subjects with PS from those with OSA would greatly facilitate timely screening and diagnosis of OSA, especially in children, which is of great importance in ameliorating the overall outcome of OSA.

SUMMARY

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

The presently-disclosed subject matter includes methods for diagnosing obstructive sleep apnea (OSA) in a subject by determining the amount of one or more biomarkers in a biological sample provided from the subject. In some embodiments, a method for diagnosing OSA is provided that comprises: providing a biological sample from the subject; determining an amount in the sample of a Urocortin (UCN) III peptide; and comparing the amount of the UCN III peptide in the sample, if present, to a control level of the UCN III peptide. In some embodiments, the subject is then diagnosed as having OSA, or a risk thereof, if there is a measurable difference in the amount of the UCN III peptide in the sample as compared to the control level. In some embodiments, a treatment is then selected or modified based on the amount of UCN III that is determined in the sample.

Further provided, in some embodiments of the presently-disclosed subject matter, is a method for determining whether to initiate or continue prophylaxis or treatment of OSA in a subject, which comprises: providing a series of biological samples over a time period from a subject; analyzing the series of biological sample to determine an amount in each of the biological samples of a UCN III peptide; and comparing any measurable change in the amounts of the UCN III peptide in each of the biological samples to thereby determine whether to initiate or continue prophylaxis or therapy of the OSA. In some embodiments, the series of biological samples includes a first biological sample, which is collected prior to the initiation of the prophylaxis or treatment for the OSA, and a second biological sample, which is collected after the initiation of prophylaxis or treatment.

In some embodiments of the presently-disclosed methods, the amount of a UCN III peptide in a biological sample obtained from a subject can be determined in conjunction with one or more additional peptides to thereby diagnose OSA in a subject. In some embodiments, the amount of a UCN III peptide is determined along with the amount of one or more peptides selected from: a Uromodulin peptide, an Orosomucoid 1 peptide, and a Kallikrein 1 peptide. In some embodiments, the amount of a UCN III peptide in a biological sample is determined along with the amounts of a Uromodulin peptide, an Orosomucoid 1 peptide, and a Kallikrein 1 peptide in a biological sample.

In some embodiments, the amounts of a UCN III peptide, a Uromodulin peptide, an Orosomucoid peptide, or a Kallikrein 1 peptide are determined by using mass spectrometry analysis, immunoassay analysis, or both. In some embodiments, the mass spectrometry analysis can be selected from liquid-chromatography mass spectrometry (LC-MS), electrospray ionization mass spectrometry (ESI-MS), matrix-assisted laser desorption time-of-flight mass spectrometry (MALDI-TOF-MS), or surface-enhanced laser desorption/ionization time-of-flight mass spectrometry (SELDI-TOF-MS). In some embodiments, the immunoassay analysis is performed by using an enzyme-linked immunosorbent assay (ELISA) or an immunoturbidimetric assay.

In some embodiments, methods for diagnosing OSA in a subject or methods for determining whether to initiate or continue prophylaxis or treatment of OSA in a subject are provided that further comprise providing an apparatus that is capable of detecting a UCN III peptide. In some embodiments, a probe for selectively binding the UCN III peptide is further provided.

Still further provided, in some embodiments of the presently-disclosed subject matter, are systems for diagnosing OSA in a subject. In some embodiments, a system for diagnosing OSA is provided that comprises: a means for obtaining a biological sample from a subject; a means for determining the amount in the sample of a UCN III peptide; and a means for comparing the amount of the UCN III peptide in the sample, if present, to a control level of the UCN III peptide such that the system is used to provide a diagnosis of OSA in a subject if there is a measurable difference in the amount of the UCN III peptide in the sample as compared to the control level.

In some embodiments, the biological sample is selected from: a urine sample, a saliva sample, a blood sample, a plasma sample, and a serum sample, which can all be readily obtained from a subject. In some embodiments, the subject is a human, such as, in some embodiments, a human child that is under that age of about 9 to about 2 years of age.

In some embodiments of the presently-disclosed subject matter, kits for diagnosing OSA in a subject are also provided. In some embodiments, a kit is provided that comprises an antibody capable of detecting a UCN III peptide and instructions for using the kit. In some embodiments, the kits further include one or more antibodies that are capable of detecting a Uromodulin peptide, an Orosomucoid 1 peptide, or a Kallikrein 1 peptide.

Advantages of the presently-disclosed subject matter will become evident to those of ordinary skill in the art after a study of the description, Figures, and non-limiting Examples in this document.

DESCRIPTION OF THE DRAWINGS

FIG. 1A includes images of 2D-DIGE gels of urinary proteins of a child with primary snoring (PS), a child with obstructive sleep apnea (OSA), and a fluorescent overlay of those two images (OVERLAY). FIGS. 1B and 1C include gel images and graphs showing the differential intensity analysis for two protein spots showing increased expression in OSA. FIGS. 1D and 1E include gel images and graphs showing the differential intensity analysis for two proteins spots showing decreased expression in OSA.

DESCRIPTION OF EXEMPLARY EMBODIMENTS

Figure 1A:
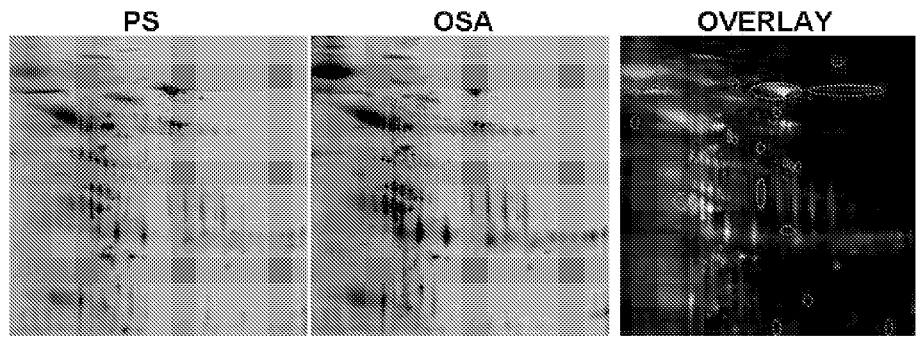
FIGS. 1A-1E are images showing two-dimensional differential in-gel electrophoretic (2D-DIGE) analysis of urinary proteins in children.
Figure 1B:
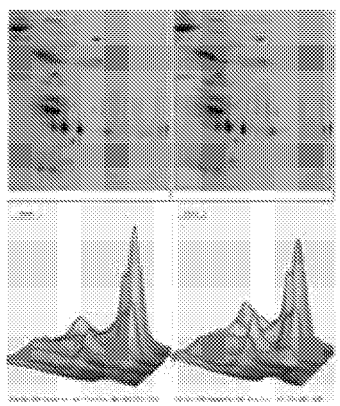
Figure 1C:
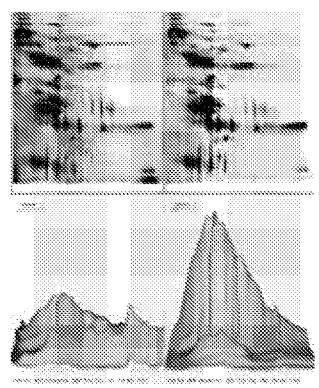
Figure 1D:
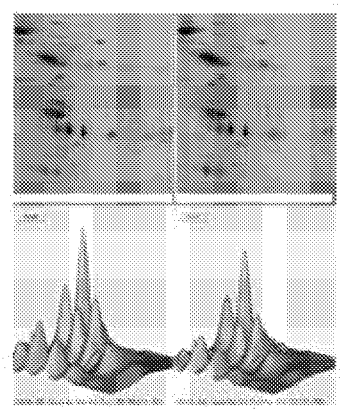
Figure 1E:
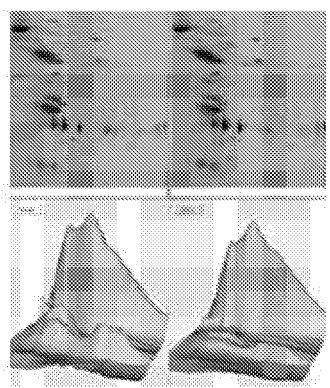

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

Peptides described herein are described with reference to GENBANK® accession numbers and SWISSPROT identification numbers. The sequences cross-referenced in the GENBANK® and SWISSPROT databases are expressly incorporated by reference as are equivalent and related sequences present in GENBANK®, SWISSPROT, or other public databases. Also expressly incorporated herein by reference are all annotations present in the GENBANK® and SWISSPROT databases associated with the sequences disclosed herein. Unless otherwise indicated or apparent the references to the GENBANK® database and the SWISSPROT database are references to the most recent version of the database as of the filing date of this application.

While the terms used herein are believed to be well understood by one of ordinary skill in the art, definitions are set forth to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a peptide" includes a plurality of such peptides, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

The terms "polypeptide", "protein", and "peptide", which are used interchangeably herein, refer to a polymer of the 20 protein amino acids, including modified amino acids (e.g., phosphorylated, glycated, etc.) and amino acid analogs, regardless of size or function. Although "protein" is often used in reference to relatively large polypeptides, and "peptide" is often used in reference to small polypeptides, usage of these terms in the art overlaps and varies. The term "peptide" as used herein refers to peptides, polypeptides, proteins and fragments of proteins, unless otherwise noted. The terms "protein", "polypeptide" and "peptide" are used interchangeably herein when referring to a gene product and fragments thereof. Thus, exemplary polypeptides include gene products, naturally occurring proteins, homologs, orthologs, paralogs, fragments and other equivalents, variants, fragments, and analogs of the foregoing.

The terms "polypeptide fragment" or "fragment", when used in reference to a polypeptide, refers to a polypeptide in which amino acid residues are absent as compared to the full-length polypeptide itself, but where the remaining amino acid sequence is usually identical to the corresponding positions in the reference polypeptide. Such deletions can occur at the amino-terminus or carboxy-terminus of the reference polypeptide, or alternatively both. A fragment can retain one or more of the biological activities of the reference polypeptide. In some embodiments, a fragment can comprise a domain or feature, and optionally additional amino acids on one or both sides of the domain or feature, which additional amino acids can number from 5, 10, 15, 20, 30, 40, 50, or up to 100 or more residues. Further, fragments can include a sub-fragment of a specific region, which sub-fragment retains a function of the region from which it is derived. When the term "peptide" is used herein, it is intended to include the full-length peptide as well as fragments of the peptide. Thus, an identified fragment of a peptide (e.g., by mass spectrometry) is intended to encompass the fragment as well as the full-length peptide. As such, determining an amount of a biomarker in a sample can include determining an amount of the full-length biomarker polypeptide, modified variants, and/or fragments thereof.

The terms "Obstructive Sleep Apnea" and "Obstructive Sleep Apnea Syndrome," are used interchangeably herein to refer to a condition that is characterized by a history of habitual snoring, and which is associated with repeated events of partial or complete obstruction of the upper airway during sleep. Obstructive Sleep Apnea (OSA) is a clinically complex syndrome affecting up to 3% of pre-pubertal children and causes subjects to experience both daytime and nighttime symptoms. As noted, the main nocturnal system is habitual snoring. However, subjects afflicted with OSA frequently experience further nocturnal symptoms including, but not limited to, respiratory pauses, noisy breathing sounds, paradoxical breathing movements, cyanosis, restless sleep, excessive diaphoresis, sleep enuresis, as well as recurring episodes gas exchange abnormalities, such as hypercapnia and hypoxemia, and frequent arousals (i.e., sleep fragmentation). As such, OSA is typically ranked at the severe end of the clinical spectrum of sleep disordered breathing.

At the other end of the clinical spectrum is a less severe condition known as habitual or primary snoring (PS), which is typically considered to be a more benign form of upper airway resistance. PS occurs in the absence of gas exchange abnormalities or evidence of snore-associated alterations in sleep architecture. Indeed, PS is a relatively frequent condition and is predicted to affect 10-12% of all school-aged children.

Currently, the ability to accurately diagnose OSA and distinguish between OSA and PS requires an overnight sleep study, or polysomnography, which is not readily available to many subjects due to the cost and the availability of a suitable sleep diagnostic facility. Thus, a subject may be afflicted with OSA for an extended period of time without an accurate diagnosis and subsequent treatment, which can thus cause the adverse consequences associated with OSA to be long-lasting or permanent. As such, the presently-disclosed subject matter provides methods and peptide biomarkers that can be utilized to diagnose OSA, and distinguish it from PS, without the need of an overnight sleep study, thereby providing earlier treatment opportunities.

Disclosed herein are methods for diagnosing OSA using peptide levels associated with OSA as biomarkers. In some embodiments, the presently-disclosed subject matter includes methods and kits for diagnosing OSA in a subject, and for determining whether to initiate or continue prophylaxis or treatment of OSA in a subject, by identifying at least one peptide biomarker associated with OSA in a biological sample from the subject.

In some embodiments, the at least one peptide biomarker that is associated with OSA is a Urocortin (UCN) III peptide. In some embodiments, the amount of a UCN III peptide in a biological sample from a subject is determined to thereby diagnose OSA in a subject. In some embodiments, a method for diagnosing OSA is provided in which the amount of a UCN III peptide is determined along with the amounts of one or more peptides selected from the group consisting of: a Uromodulin peptide, an Orosomucoid 1 peptide, and a Kallikrein 1 peptide. In some embodiments, a method for diagnosing OSA is provided in which the amounts of a UCN III peptide, a Uromodulin peptide, an Orosomucoid 1 peptide, and a Kallikrein 1 peptide are each determined in a biological sample obtained from a subject. A list of these exemplary peptide biomarkers of OSA, as well as exemplary GENBANK® Accession and SWISSPROT Identification Numbers for each of these peptide biomarkers, is provided in Table 1 below:

TABLE 1

Exemplary Biomarkers Associated with OSA.

| Peptide Name | GENBANK® Accession Number | SWISSPROT Identification Number |
|---|---|---|
| Urocortin III | AAK67317 | Q969E3 |
| Uromodulin | AAL27853 | P07911 |
| Orosomucoid 1* | EAW87416 | P02763 |
| Kallikrein 1 | AAH05313 | P06870 |

*Orosomucoid 1 can also be referred to as Alpha-1-acid glycoprotein 1.

With regard to the presently-disclosed subject matter, the exemplary human peptides provided in Table 1 are not intended to limit the presently-disclosed subject matter to human polypeptide biomarkers. Rather, the present subject matter encompasses peptide biomarkers across animal species that are associated with OSA. In addition, standard gene/protein nomenclature guidelines generally stipulate human gene name abbreviations are capitalized and italicized, and protein name abbreviations are capitalized, but not italicized. Further, standard gene/protein nomenclature guidelines generally stipulate mouse, rat, and chicken gene name abbreviations italicized with the first letter only capitalized, and protein name abbreviations capitalized, but not italicized. In contrast, the gene/protein nomenclature used herein when referencing specific biomarkers uses first letter capitalized for the biomarker name, but is intended to be inclusive of genes (including mRNAs and cDNAs) and proteins across animal species.

A "biomarker" is a molecule useful as an indicator of a biologic state in a subject. With reference to the present subject matter, the biomarkers disclosed herein can be polypeptides (e.g., UCN III, Uromodulin, Orosomucoid 1, or Kallikrein 1 peptides) that exhibit a change in expression or state, which can be correlated with the risk of developing, the presence of, or the progression of OSA in a subject. In addition, the peptide biomarkers disclosed herein are inclusive of messenger RNAs (mRNAs) encoding the peptide biomarkers associated with OSA, as measurement of a change in expression of an mRNA can be correlated with changes in expression of the polypeptide encoded by the mRNA. As such, determining an amount of a peptide biomarker associated with OSA in a biological sample is inclusive of determining an amount of the peptide biomarker, including fragments thereof, and/or an amount of an mRNA encoding the peptide biomarker either by direct or indirect (e.g., by measure of a complementary DNA (cDNA) synthesized from the mRNA) measurement of the mRNA.

As noted, in some embodiments of the presently-disclosed subject matter, a method for diagnosing OSA in a subject is provided. The terms "diagnosing" and "diagnosis," as used herein, refer to methods by which the skilled artisan can estimate and even determine whether or not a subject is suffering from a given disease or condition. The skilled artisan often makes a diagnosis on the basis of one or more diagnostic indicators, such as for example a biomarker, the amount (including presence or absence) of which is indicative of the presence, severity, or absence of the condition.

Along with diagnosis, clinical disease prognosis is also an area of great concern and interest. If a more accurate prognosis can be made, appropriate therapy, and in some instances less severe therapy for the patient can be chosen. As such, "making a diagnosis" or "diagnosing", as used herein, is further inclusive of determining a prognosis, which can provide for predicting a clinical outcome (with or without medical treatment), selecting an appropriate treatment (or whether treatment would be effective), or monitoring a current treatment and potentially changing the treatment, based on the measure of levels of diagnostic biomarkers disclosed herein.

The phrase "determining a prognosis" as used herein refers to methods by which the skilled artisan can predict the course or outcome of a condition in a subject. The term "prognosis" does not refer to the ability to predict the course or outcome of a condition with 100% accuracy, or even that a given course or outcome is predictably more or less likely to occur based on the presence, absence or levels of test biomarkers. Instead, the skilled artisan will understand that the term "prognosis" refers to an increased probability that a certain course or outcome will occur; that is, that a course or outcome is more likely to occur in a subject exhibiting a given condition, when compared to those individuals not exhibiting the condition. For example, in individuals not exhibiting the condition (e.g., not expressing the biomarker or expressing it at a reduced level), the chance of a given outcome may be about 3%. In certain embodiments, a prognosis is about a 5% chance of a given outcome, about a 7% chance, about a 10% chance, about a 12% chance, about a 15% chance, about a 20% chance, about a 25% chance, about a 30% chance, about a 40% chance, about a 50% chance, about a 60% chance, about a 75% chance, about a 90% chance, or about a 95% chance.

The skilled artisan will also understand that associating a prognostic indicator with a predisposition to an adverse outcome is a statistical analysis. For example, a UCN III peptide level (e.g., quantity of expression in a sample) of greater than a control level in some embodiments can signal that a subject is more likely to suffer from OSA than subjects with a level less than or equal to the control level, as determined by a level of statistical significance. Alternatively, in some embodiments, a UCN III peptide level of less than or equal to a control level can signal that a subject does not suffer from OSA. Additionally, a change in UCN III peptide concentration from baseline levels can be reflective of subject prognosis, and the degree of change in marker level can be related to the severity of adverse events. Statistical significance is often determined by comparing two or more populations, and determining a confidence interval and/or a p value. See, e.g., Dowdy and Wearden, Statistics for Research, John Wiley & Sons, New York, 1983, incorporated herein by reference in its entirety. Preferred confidence intervals of the present subject matter are 90%, 95%, 97.5%, 98%, 99%, 99.5%, 99.9% and 99.99%, while preferred p values are 0.1, 0.05, 0.025, 0.02, 0.01, 0.005, 0.001, and 0.0001.

In other embodiments, a threshold degree of change in the level of a prognostic or diagnostic biomarker can be established, and the degree of change in the level of the indicator in a biological sample can simply be compared to the threshold degree of change in the level. A preferred threshold change in the level for markers of the presently-disclosed subject matter is about 5%, about 10%, about 15%, about 20%, about 25%, about 30%, about 50%, about 75%, about 100%, about 150%, or more. In yet other embodiments, a "nomogram" can be established, by which a level of a prognostic or diagnostic indicator can be directly related to an associated disposition towards a given outcome. The skilled artisan is acquainted with the use of such nomograms to relate two numeric values with the understanding that the uncertainty in this measurement is the same as the uncertainty in the marker concentration because individual sample measurements are referenced, not population averages.

In some embodiments of the presently-disclosed subject matter, multiple determinations of one or more diagnostic or prognostic peptides associated with OSA, such as UCN III, can be made, and a temporal change in the biomarker peptides can be used to monitor the progression of disease and/or efficacy of appropriate therapies directed against the disease. In such an embodiment, for example, one might expect to see a decrease or an increase in the UCN III peptide(s) over time during the course of effective therapy. Thus, the presently disclosed subject matter provides, in some embodiments, a method for determining whether to initiate or continue treatment of OSA in a subject. In some embodiments, the method comprises determining an amount of a UCN III peptide in biological samples collected from the subject at a plurality of different time points and comparing any measurable changes in the amounts of the UCN III peptide in the samples collected at different time points. For example, a first time point can be selected prior to initiation of a treatment and a second time point can be selected at some time after initiation of the treatment. UCN III peptide levels can be measured in each of the samples taken from different time points and qualitative and/or quantitative differences noted. A change in the amounts of the UCN III peptide levels from the first and second samples can be correlated with determining treatment efficacy and/or progression of the disease in the subject.

In some embodiments, a method for determining whether to initiate or continue prophylaxis or treatment of OSA in a subject is provided that further comprises determining an amount in a biological sample of a UCN III peptide in conjunction with one or more peptides selected from a Uromodulin peptide, an Orosomucoid 1 peptide, and a Kallikrein 1 peptide at different time points such that measurable changes in the various peptides over time can then be compared. For example, in some embodiments, the amount of a UCN III peptide is determined along with a Uromodulin peptide, an Orosomucoid 1 peptide, and a Kallikrein 1 peptide at different time points and qualitative and/or quantitative differences in the levels of each peptide are noted. Similar to the methods described above with respect to identifying UCN III independently of other peptide biomarkers, a change in the amounts of the UCN III, Uromodulin, Orosomucoid 1 peptide, and/or Kallikrein 1 peptide levels in the samples that are collected at different time points can be correlated with determining treatment efficacy and/or progression of the disease in the subject.

The terms "correlated" and "correlating," as used herein in reference to the use of diagnostic and prognostic biomarkers, refers to comparing the presence or quantity of the biomarker in a subject to its presence or quantity in subjects known to suffer from a given condition (e.g., OSA); or in subjects known to be free of a given condition, i.e. "normal individuals." For example, a UCN III peptide level in a biological sample can be compared to a level known to be associated with OSA. The sample's UCN III peptide level is said to have been correlated with a diagnosis; that is, the skilled artisan can use the UCN III peptide level to determine whether the subject suffers from OSA, and respond accordingly. Alternatively, the sample's UCN III peptide level can be compared to a control UCN III peptide level known to be associated with a good outcome (e.g., the absence of OSA), such as an average level found in a population of normal subjects.

In certain embodiments, a diagnostic biomarker is correlated to a condition or disease by merely its presence or absence. In other embodiments, a threshold level of a diagnostic biomarker can be established, and the level of the indicator in a subject sample can simply be compared to the threshold level. In yet other embodiments, multiple determinations of one or more diagnostic biomarkers can be made, and a temporal change in the marker can be used to determine a diagnosis, including a prognosis.

The skilled artisan will understand that, while in certain embodiments comparative measurements can be made of the same diagnostic marker at multiple time points, one can also measure a given marker at one time point, and a second marker at a second time point, and a comparison of these markers can provide diagnostic information.

In some embodiments, a method for diagnosing OSA in a subject comprises providing a biological sample from the subject; determining an amount in the sample of a UCN III peptide; and comparing the amount of the UCN III peptide in the sample, if present, to a control level of the UCN III peptide. If there is a measurable difference in the amount of the UCN III peptide in the sample as compared to a control level, the subject can then be diagnosed as having OSA or a risk thereof.

Disclosed herein are data demonstrating that UCN III peptide levels in a biological sample obtained from a subject can be utilized as a biomarker for diagnosing subjects with OSA. Further disclosed herein, however, are additional data and information demonstrating that while UCN III peptide levels can be used to accurately diagnose OSA, the determination of an amount of a UCN III peptide level in a biological sample along with the amount of a Uromodulin peptide, an Orosomucoid 1 peptide, and a Kallikrein 1 peptide in the same biological sample can allow for a diagnosis of OSA with increased sensitivity and specificity. As such, in some embodiments, a method for diagnosing OSA in a subject is provided that further comprises determining an amount in the sample of one or more peptides selected from: a Uromodulin peptide, an Orosomucoid 1 peptide, and a Kallikrein 1 peptide. In some embodiments, the amounts of a Uromodulin peptide, an Orosomucoid 1 peptide, and a Kallikrein 1 peptide in a biological sample are determined along with the amount of a UCN III peptide to thereby diagnose a particular subject as having OSA.

With regard to the step of providing a biological sample from the subject, the term "biological sample" as used herein refers to any body fluid or tissue potentially comprising a peptide biomarker associated with OSA, such as those disclosed herein. In some embodiments, for example, the biological sample can be a urine sample, a saliva sample, a blood sample, a serum sample, a plasma sample, or sub-fractions thereof.

Turning now to the step of determining an amount of a peptide biomarker associated with OSA in the biological sample, various methods known to those skilled in the art can be used to identify a peptide biomarker in the provided biological sample. In some embodiments, determining the amount of a peptide biomarker in samples comprises using an RNA measuring assay to measure mRNA encoding peptide biomarkers associated with OSA in the sample and/or using a protein measuring assay to measure amounts of the peptides biomarkers in the sample.

In certain embodiments, the amounts of the peptide biomarkers can be determined by probing for mRNA of the peptide biomarker (e.g., UCN III, Uromodulin, Orosomucoid 1, and/or Kallikrein 1) in the sample using any RNA identification assay known to those skilled in the art. Briefly, RNA can be extracted from the sample, amplified, converted to cDNA, labeled, and allowed to hybridize with probes of a known sequence, such as known RNA hybridization probes (selective for mRNAs encoding the peptide biomarkers) immobilized on a substrate, e.g., array, or microarray, or quantitated by real time PCR (e.g., quantitative real-time PCR, such as available from Bio-Rad Laboratories, Hercules, Calif., U.S.A.). Because the probes to which the nucleic acid molecules of the sample are bound are known, the molecules in the sample can be identified. In this regard, DNA probes for one or more of the mRNAs encoding the biomarker peptides of the presently-disclosed subject matter can be immobilized on a substrate and provided for use in practicing a method in accordance with the present subject matter.

With regard to determining amounts of the biomarker peptides associated with OSA disclosed herein in samples, mass spectrometry and/or immunoassay devices and methods can be used to measure the peptides in samples, although other methods are well known to those skilled in the art as well. See, e.g., U.S. Pat. Nos. 6,143,576; 6,113,855; 6,019,944; 5,985,579; 5,947,124; 5,939,272; 5,922,615; 5,885,527; 5,851,776; 5,824,799; 5,679,526; 5,525,524; and 5,480,792, each of which is hereby incorporated by reference in its entirety. Immunoassay devices and methods can utilize labeled molecules in various sandwich, competitive, or non-competitive assay formats, to generate a signal that is related to the presence or amount of an analyte of interest. Additionally, certain methods and devices, such as biosensors and optical immunoassays, can be employed to determine the presence or amount of analytes without the need for a labeled molecule. See, e.g., U.S. Pat. Nos. 5,631,171; and 5,955,377, each of which is hereby incorporated by reference in its entirety.

Thus, in certain embodiments of the presently-disclosed subject matter, the peptide biomarkers of the presently-disclosed subject matter are analyzed using an immunoassay.

The presence or amount of a peptide biomarker (e.g., UCN III) can be determined using antibodies or fragments thereof specific for each marker and detecting specific binding. For example, in some embodiments, an antibody specifically binds UCN III, which is inclusive of antibodies that bind the full-length peptide or a fragment thereof.

Any suitable immunoassay can be utilized, for example, enzyme-linked immunoassays (ELISA), radioimmunoassays (RIAs), competitive binding assays, immunoturbidimetric assays, and the like. Specific immunological binding of the antibody to the marker can be detected directly or indirectly. Direct labels include fluorescent or luminescent tags, metals, dyes, radionucleotides, and the like, attached to the antibody. Indirect labels include various enzymes well known in the art, such as alkaline phosphatase, horseradish peroxidase and the like.

The use of immobilized antibodies or fragments thereof specific for the peptides biomarkers of the presently disclosed subject matter (e.g., UCN III, Uromodulin, Orosomucoid 1, and/or Kallikrein 1) is also contemplated by the presently-disclosed subject matter. The antibodies can be immobilized onto a variety of solid supports, such as magnetic or chromatographic matrix particles, the surface of an assay plate (such as microtiter wells), pieces of a solid substrate material (such as plastic, nylon, paper), and the like. An assay strip can be prepared by coating the antibody or a plurality of antibodies in an array on a solid support. This strip can then be dipped into the test biological sample and then processed quickly through washes and detection steps to generate a measurable signal, such as for example a colored spot.

In some embodiments, mass spectrometry (MS) analysis can be used alone or in combination with other methods (e.g., immunoassays) to determine the presence and/or quantity of the peptide biomarker of interest (e.g., UCN III, Uromodulin, Orosomucoid 1, or Kallikrein 1) in a biological sample. In some embodiments, the MS analysis comprises liquid chromatography-mass spectrometry (LC-MS). In some embodiments, the MS analysis comprises matrix-assisted laser desorption/ionization time-of-flight MS analysis (MALDI-TOF-MS), such as for example direct-spot MALDI-TOF or liquid chromatography MALDI-TOF mass spectrometry analysis. In some embodiments, the MS analysis comprises electrospray ionization MS (ESI-MS), such as for example liquid chromatography (LC) ESI-MS. Mass spectrometry analysis can be accomplished using commercially-available spectrometers, such as for example triple quadrupole mass spectrometers. In some embodiments, the MS analysis comprises surface enhanced laser desorption/ionization time-of-flight mass spectrometry analysis (SELDI-TOF-MS). Methods for utilizing MS analysis to detect the presence and quantity of biomarker peptides in biological samples are known in the art. See, for example, U.S. Pat. Nos. 6,925,389; 6,989,100; and 6,890,763 for further guidance, as well as Slominski, et al., *Journal of Clinical Endocrinology and Metabolism*, 2000 February; 85(2): p. 815-823, each of which are incorporated herein by this reference.

Although certain embodiments of the methods disclosed herein only call for a qualitative assessment of the presence or absence of the one or more biomarkers in the biological sample, other embodiments of the methods call for a quantitative assessment of the amount of each of the one or more markers in the biological sample. Such quantitative assessments can be made, for example, using one of the above mentioned methods, as will be understood by those skilled in the art.

In certain embodiments of the presently-disclosed methods, a subject is diagnosed as having OSA upon determining, in a biological sample obtained from the subject, an amount of a UCN III peptide, either alone or in combination with the amounts of one or more peptides selected from a Uromodulin peptide, an Orosomucoid 1 peptide, and a Kallikrein 1 peptide. In other embodiments of the method, the determination of an amount of a Urocortin III peptide, either alone or in combination with one or more peptides selected from a Uromodulin peptide, an Orosomucoid 1 peptide, and a Kallikrein 1 peptide, in a biological sample obtained from the subject results in the subject being identified as having a risk of OSA.

In certain embodiments of the method, it can be desirable to include a control sample that is analyzed concurrently with the biological sample, such that the results obtained from the biological sample can be compared to the results obtained from the control sample. Additionally, it is contemplated that standard curves can be provided, with which assay results for the biological sample can be compared. Such standard curves present levels of protein markers as a function of assay units, i.e., fluorescent signal intensity, if a fluorescent signal is used. Using samples taken from multiple donors, standard curves can be provided for control levels of the one or more biomarkers in normal tissue.

The analysis of biomarkers can be carried out separately or simultaneously with additional biomarkers within one test sample. For example, several biomarkers (e.g., UCN III, Uromodulin, Orosomucoid 1, and Kallikrein peptides) can be combined into one test for efficient processing of multiple samples and for potentially providing greater diagnostic and/or prognostic accuracy. In addition, one skilled in the art would recognize the value of testing multiple samples (for example, at successive time points) from the same subject. Such testing of serial samples can allow the identification of changes in marker levels over time. Increases or decreases in marker levels, as well as the absence of change in marker levels, can provide useful information about the disease status that includes, but is not limited to identifying the approximate time from onset of the event, the appropriateness of drug therapies, the effectiveness of various therapies, and identification of the subject's outcome, including risk of future events.

As noted, depending on the embodiment of the method, identification of the peptides biomarkers associated with OSA can be a qualitative determination of the presence or absence of the biomarkers, or it can be a quantitative determination of the concentration of the peptide biomarkers. In this regard, in some embodiments, the step of identifying the subject as having OSA or a risk thereof requires that certain threshold measurements are made, i.e., the levels of a peptide biomarker in the biological sample exceeds or is below the control level. In certain embodiments of the method, the control level is any detectable level of the peptide biomarkers. In other embodiments of the method where a control sample is tested concurrently with the biological sample, the control level is the level of detection in the control sample. In other embodiments of the method, the control level is based upon and/or identified by a standard curve. In other embodiments of the method, the control level is a specifically identified concentration, or concentration range. As such, the control level can be chosen, within acceptable limits that will be apparent to those skilled in the art, based in part on the embodiment of the method being practiced and the desired specificity, etc.

Further provided, in some embodiments of the presently-disclosed subject matter, are systems for diagnosing OSA in a subject. In some embodiments, a system for diagnosing OSA in a subject is provided that comprises a means for obtaining a biological sample from a subject; a means for determining the amount in the sample of a UCN III peptide; and a means for comparing the amount of a UCN III peptide in a sample, if present, to a control level of the UCN III peptide such that the subject can be diagnosed as having OSA if there is a measurable difference in the amount of the UCN III peptide in the sample as compared to a control level. In other embodiments, various means for determining the amount, as well as means for comparing the amount, of a Uromodulin peptide, an Orosomucoid 1 peptide, and a Kallikrein 1 peptide can be provided in an exemplary system such that the amounts of one or more of the foregoing peptides can also be determined.

The means for obtaining a biological sample from a subject in accordance with the presently-disclosed systems can comprise any means known to those of ordinary skill in the art which can be used for obtaining a particular biological sample from a subject. For example, to obtain a blood sample from a subject, a hypodermic needle or other such suitable device can be used to collect a blood sample from an artery or vein of a subject. As another example, in embodiments where a urine or saliva sample is obtained from a subject, the means for obtaining the sample can comprise a cup or other suitable container into which the urine or saliva sample can be deposited.

With respect to the means for determining an amount of a peptide biomarker associated with OSA in a subject, in some embodiments, the means for determining the amount of the peptide biomarker can comprise an apparatus, such as a mass spectrometry apparatus, or a probe for selectively binding a peptide biomarker associated with OSA. For example, in some embodiments, the probe can be an antibody that selectively binds to the peptide biomarker. As another example, in other embodiments where the amount of a peptide biomarker is determined by measuring the amount of mRNA of the peptide biomarker, the means for determining the amount of the peptide biomarker can be an RNA hybridization probe that is selective for the mRNA encoding the peptide biomarker.

Still further provided, in some embodiments of the presently-disclosed subject matter, are kits for the analysis of biomarkers that comprise antibodies having specificity for one or more biomarkers associated with OSA. Such a kit can comprise devices and reagents for the analysis of at least one test sample. In some embodiments, the kits further comprise instructions for using the kit. Optionally, in some embodiments, the kits can also contain one or more reagents or devices for converting a biomarker level to a diagnosis or prognosis of the subject.

In some embodiments, a kit is provided that that comprises an antibody capable of detecting a UCN III peptide in a subject and instructions for using the kit. In other embodiments, a kit is provided that further comprises one or more antibodies capable of detecting one or more peptides selected from a Uromodulin peptide, an Orosomucoid 1 peptide, and a Kallikrein 1 peptide. In some embodiments, a kit is provided that includes antibodies capable of detecting a UCN III peptide, a Uromodulin peptide, an Orosomucoid 1 peptide, and a Kallikrein 1 peptide such that the levels of each of the peptides can be detected in a biological sample obtained from a subject.

With respect to the presently-disclosed subject matter, the subject can be a vertebrate subject. A vertebrate subject can be warm-blooded; a warm-blooded vertebrate subject can be a mammal. A mammalian subject can be a human. In some embodiments, a human subject can be a child. A child can be a human that is under the age of about 18, 17, 16, 15, 14, 13, 12, 11, 10, 9, 8, 7, 6, 5, 4, 3, 2, or 1. In some embodiments, the subject is a human child that is under the age of about 9 to about 2 years of age.

As used herein, the term "subject" includes both human and animal subjects. Thus, veterinary therapeutic uses are provided in accordance with the presently-disclosed subject matter. As such, the presently-disclosed subject matter provides for the diagnosis of mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Also provided is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economic importance to humans. Thus, also provided is the treatment of livestock, including, but not limited to, domesticated swine, ruminants, ungulates, horses (including race horses), poultry, and the like.

The practice of the presently-disclosed subject matter can employ, unless otherwise indicated, conventional techniques of cell biology, cell culture, molecular biology, transgenic biology, microbiology, recombinant DNA, and immunology, which are within the skill of the art. Such techniques are explained fully in the literature. See, e.g., Molecular Cloning A Laboratory Manual (1989), 2nd Ed., ed. by Sambrook, Fritsch and Maniatis, eds., Cold Spring Harbor Laboratory Press, Chapters 16 and 17; U.S. Pat. No. 4,683,195; DNA Cloning, Volumes I and II, Glover, ed., 1985; Oligonucleotide Synthesis, M. J. Gait, ed., 1984; Nucleic Acid Hybridization, D. Hames & S. J. Higgins, eds., 1984; Transcription and Translation, B. D. Hames & S. J. Higgins, eds., 1984; Culture Of Animal Cells, R. I. Freshney, Alan R. Liss, Inc., 1987; Immobilized Cells And Enzymes, IRL Press, 1986; Perbal (1984), A Practical Guide To Molecular Cloning; See Methods In Enzymology (Academic Press, Inc., N.Y.); Gene Transfer Vectors For Mammalian Cells, J. H. Miller and M. P. Calos, eds., Cold Spring Harbor Laboratory, 1987; Methods In Enzymology, Vols. 154 and 155, Wu et al., eds., Academic Press Inc., N.Y.; Immunochemical Methods In Cell And Molecular Biology (Mayer and Walker, eds., Academic Press, London, 1987; Handbook Of Experimental Immunology, Volumes I-IV, D. M. Weir and C. C. Blackwell, eds., 1986.

The presently-disclosed subject matter is further illustrated by the following specific but non-limiting examples.

EXAMPLES

Example 1

Subject Selection and Diagnosis of Obstructive Sleep Apnea by Overnight Polysomnography Children who were referred for evaluation of habitual snoring and suspected sleep disordered breathing were recruited. As controls, children from the community who had no history of any chronic or acute disorder, and who did not snore, were also invited to participate. Exclusion criteria for all subjects included the presence of genetic or systemic disorders, significant neuromuscular diseases, renal disease, or any acute infectious processes. All parents completed a detailed intake clinical questionnaire. Height and weight and vital signs were recorded for each child, and body mass index (BMI) z score was calculated using CDC 2000 growth standards and associated online software. A BMI z-score>1.65 (>95$^{th}$ percentile) was considered as fulfilling obese criteria.

All subjects underwent overnight polysomnography (PSG) using standard techniques (18). Children were studied for up to 12 hours in a quiet, darkened room maintained at an ambient temperature of 24°. No medication was used to induce sleep. During that time, the following parameters were measured: chest and abdominal wall movement by inductance plethysmography; heart rate by electrocardiography; and air flow by a side-stream end-tidal capnograph that also provides breath-by-breath assessment of end-tidal carbon dioxide levels (BCI SC-300, Menomonee Falls, Wis.), a nasal pressure cannula, and an oronasal thermistor. Arterial pulse oxygen saturation ($SpO_2$) was assessed by pulse oximetry (Nellcor N 100 (Nellcor Inc, Hayward, Calif.)), with simultaneous recording of the pulse waveform. The bilateral electro-oculogram, 8 channels of electroencephalogram (2 frontal, 2 occipital, 2 temporal, and 2 central leads), chin and anterior tibial electromyograms, and analog output from a body position sensor were also monitored. All measures were digitized using a commercially available system (Sandman, Nellcor Puritan Bennett, Kanata, ON, Canada, or Stellate Instruments, Montreal, QC, Canada). Tracheal sound was monitored with a microphone sensor, and a digital time-synchronized video recording was performed. A sleep technician followed patient behavior and confirmed sleep position by an infrared camera located inside the room. All of the studies were initially scored by a certified technician and were then reviewed by a physician who was experienced in pediatric PSG and underwent training in an accredited fellowship program.

Sleep architecture was assessed by standard techniques (19). Central, obstructive, and mixed apneic events were counted. Obstructive apnea was defined as the absence of airflow with continued chest wall and abdominal movement for duration of at least 2 breaths (18). Hypopneas were defined as a decrease in oronasal flow of ≥50% with a corresponding decrease in $SpO_2$ of 3% or more and/or an arousal (18). The obstructive apnea hypopnea index (OAHI) was defined as the number of obstructive apneas and hypopneas per hour of total sleep time (TST). Arousals were identified as defined by the American Sleep Disorders Association Task Force report (20).

Subjects were then divided into 3 groups according to whether they had habitual or primary snoring (PS) or not and their sleep study findings. Criteria for obstructive sleep apnea (OSA) included an obstructive apnea index (AI) greater than 1/h TST, and/or an obstructive apnea-hypopnea index (AHI) greater than 2/h TST with a nadir oxygen saturation value less than 92%. PS children were defined as children with habitual snoring and an AHI less than or equal to 2/h TST, with no evidence of any alterations in arousal indices and normal gas exchange during sleep. Control children were non-snoring children that showed similar sleep finding criteria as those with PS.

A total of 120 subjects between the ages of 2 and 9 years were studied. Their demographic characteristics (Table 2) revealed that there were no significant differences in age, sex, ethnicity, or BMI distribution among the 3 groups, and that the frequency of asthma and allergies was also similar among the 3 groups.

TABLE 2

Demographic characteristics of 60 children with OSA, 30 matched children with primary snoring (PS), and 30 matched controls.

| | OSA (n = 60) | PS (n = 30) | CO (n = 30) |
|---|---|---|---|
| Mean age (years) | 6.6 ± 0.7 | 6.7 ± 0.4 | 6.6 ± 0.4 |
| Male gender (n) | 32 | 16 | 16 |
| BMI z score | 1.18 ± 0.03 | 1.01 ± 0.04 | 0.98 ± 0.04 |
| Systolic Blood Pressure (mmHg) | 106.2 ± 4.1 | 103.2 ± 3.9 | 102.8 ± 3.8 |
| Diastolic Blood pressure (mmHg) | 68.9 ± 2.7 | 66.8 ± 2.6 | 65.9 ± 3.1 |
| Ethnicity | | | |
| African American | 20 | 10 | 10 |
| White Non-Hispanic | 40 | 20 | 20 |
| Maternal educational attainment | | | |
| College or higher | 38 | 19 | 20 |
| High School or lower | 22 | 11 | 10 |
| Maternal smoking | | | |
| Yes | 23 | 11 | 9 |
| No | 37 | 19 | 11 |
| Asthma | 7 | 4 | 3 |
| Allergies | 12 | 6 | 6 |

Furthermore, as expected from the study design, there were significant differences in several PSG measures in the OSA group, compared to the other 2 groups, but no differences between PS and CO (Table 3).

TABLE 3

Polysomnographic findings in 60 children with OSA, 30 matched children with primary snoring (PS), and 30 matched controls.

| | OSA (n = 60) | PS (n = 30) | CO (n = 30) |
|---|---|---|---|
| Sleep efficiency (%) | 88.6 ± 6.0 | 91.6 ± 7.9 | 90.7 ± 8.8 |
| Sleep latency (min) | 17.3 ± 14.8* | 24.7 ± 22.8 | 27.4 ± 19.9 |
| REM latency (min) | 112.7 ± 49.1 | 121.1 ± 38.4 | 124.1 ± 47.7 |
| Stage 1 (% TST) | 10.6 ± 9.2 | 8.3 ± 4.9 | 7.8 ± 5.9 |
| Stage 2 (% TST) | 48.9 ± 6.6 | 42.4 ± 9.6 | 41.3 ± 9.6 |
| SWS (% TST) | 19.6 ± 7.0* | 23.7 ± 6.4 | 25.2 ± 7.1 |
| REM (% TST) | 22.4 ± 6.1 | 24.6 ± 7.1 | 26.6 ± 7.8 |
| Spontaneous arousal index (/hrTST) | 4.4 ± 3.4** | 8.2 ± 2.8 | 7.5 ± 2.2 |
| Respiratory arousal index (/hrTST) | 10.4 ± 10.1*** | 1.8 ± 0.4 | 0.7 ± 0.5 |
| AHI (/hr TST) | 12.4 ± 5.6*** | 0.8 ± 0.4 | 0.4 ± 0.3 |
| Mean $SpO_2$ (%) | 95.7 ± 1.9** | 97.8 ± 0.7 | 98.6 ± 0.4 |
| $SpO_2$ nadir (%) | 78.6 ± 6.3*** | 93.8 ± 1.9 | 94.8 ± 1.4 |

Example 2

Differential In-Gel Electrophoresis and Mass Spectrometry Analysis of Biomarkers in Obstructive Sleep Apnea To identify and assess peptide biomarkers for OSA, the first morning void was collected on the day following the sleep study. Urine samples (20 ml) were collected in 1 ml of protease-inhibitor cocktail (0.1 mg/ml leupeptin, 0.1 mg/ml phenylmethylsulfonyl fluoride (PMSF) and 1 mM sodium azide in 1M Tris, pH 6.8) and were stored at −80° C. until analysis.

To analyze the urine samples using two-dimensional differential in-gel electrophoreses (2D-DIGE), the samples were first centrifuged at 1000×g for 5 minutes and passed through 0.34 mm Whatman chromatography paper in order to remove cell debris and nuclei. The supernatants were then subjected to centrifugation (12,000 RPM for five minutes), and the resulting pellets were resuspended in 200 μl 2-D cell lysis buffer of the following composition: 30 mmol/L Tris-HCl, pH 8.8, containing 7 mol/L urea, 2 mol/L thiourea, and 4% 3-[(3-cholamidopropyl)dimethylammonio]propanesulfonate [CHAPS]). These procedures were performed at 4° C. The protein concentrations were measured using a protein assay kit (Bio-Rad, Hercules, Calif.).

To label proteins (analytical gel), 30 μg of each of the protein samples were incubated with 0.7 μl of diluted CYDYE™ (1:5 diluted in dimethylformamide from 1 nmol/μstock, GE Health care, Piscataway, N.J.) at 4° C. for 30 minutes. The labeling was stopped by adding 0.7 μl of 10 mmol/L L-Lysine and incubating at 4° C. for 15 minutes. The labeled samples were then mixed together, and an equal volume of 2×2-D sample buffer (8 mol/L urea, 4% CHAPS, 20 mg/ml dithiothreitol [DTT], 2% pharmalytes and trace amount of bromophenol blue) and 100 μl of de-streak solution (GE Healthcare) were added. The total sample volume was adjusted to 260 μl by adding rehydration buffer (7 mol/L urea, 2 mol/L thiourea, 4% CHAPS, 20 mg/ml DTT, 1% pharmalytes, and trace amount of bromophenol blue).

The samples were then incubated at room temperature for 10 minutes on a shaker and centrifuged for 10 minutes at 16,000×g. After centrifugation, the supernatants were then loaded onto a 13 cm immobilized pH gradient strip holder (GE Healthcare). Thirteen cm immobilized pH gradient strips (pH 3 to 10) were put on the loaded samples and 1 ml of mineral oil was added. Isoelectric focusing were done following the protocol provided by the manufacturer (GE Healthcare). On completion of the isoelectric focusing, the strips were equilibrated in buffer 1 (50 mmol/L Tris-HCl, pH 8.8, containing 6 mol/L urea, 30% glycerol, 2% SDS, trace amount of bromophenol blue, and 10 mg/ml DTT) for 15 minutes and buffer 2 (50 mmol/L Tris-HCl, pH 8.8, containing 6 mol/L urea, 30% glycerol, 2% SDS, trace amount of bromophenol blue, and 45 mg/ml DTT) for 10 minutes with gentle agitation. The immobilized pH gradient strips were then rinsed in the SDS-gel running buffer, transferred to a SDS-polyacrylamide gel (10.5% SDS-gel prepared using low florescent glass plates) and sealed with 0.5% (w/v) agarose solution (in SDS-gel running buffer). The electrophoresis was performed at room temperature until the dye fronts ran out of the gels. Image scans were then performed immediately following the gel electrophoresis using Typhoon TRIO (Amersham BioSciences, Piscataway, N.J.). The scanned images were then analyzed by Image Quant software (version 5.0, Amersham BioSciences), and subjected to in-gel analysis and cross-gel analysis using DeCyder software version 6.0 (Amersham BioSciences). The ratio change of the protein differential expression was obtained from in-gel DeCyder software analysis.

The analytical gels for the 2D-DIGE were run in duplicate with a total of 150 μg of proteins being loaded on each gel. Further, in these experiments, a total of 150 2D-DIGE gel experiments were performed so as to pair the 60 samples from OSA with either PS or CO, and also to pair CO and PS samples. In addition, 38 additional 2D-DIGE gels were performed to ascertain reproducibility and consistency of the findings.

Upon analysis of the results from these experiments, the overall number of detectable protein spots ranged from 713 to 789 in all urine samples (FIG. 1). In particular, analysis of differentially expressed species revealed the presence of 28 prominently differentially expressed spots, of which 23 were consistently present across all gels.

To further analyze and obtain the identity of these 23 consistent protein spots on the gels, preparatory gels loaded with a total of 500 μg of proteins along with labeled proteins were run to pick spots. Protein spots were selected based on a cut-off of a 1.5 fold change on the 2D-gels, and were picked by an Ettan Spot Picker (Amersham BioSciences) and subjected to in-gel trypsin digestion, peptide extraction, and desalting before matrix-assisted laser desorption/ionization time-of-flight mass spectroscopy (MS; ABI 4700, Applied Biosystems, Foster City, Calif.). A GPS EXPLORER™ (Applied Biosystems) workstation was used to search the database to match both MS and MS/MS data to proteins in database. Spectral data were also converted into ".dta" files (DTA's) and searched against the IPI human non-redundant database using the Open Mass Spectrometry Search Algorithm (OMSSA; from NCBI); e-value cutoff was 0.01. All matched sequences were manually validated.

The analysis of the 23 consistent spots was conducted on at least 8 separate gels for each spot. Upon completion of these experiments, 12 non-redundant proteins were able to be consistently identified. In addition to these 12 non-redundant proteins, 4 additional proteins, namely gelsolin, perlecan, albumin, and immunoglobulin were also confirmed as being differentially expressed, as previously reported (16). A list of the 12 novel non-redundant proteins that were identified with high level of confidence on the basis of amino acid sequencing of 12 to 26 peptides per digested spot is presented in Table 4.

TABLE 4

Urinary Proteins Altered in OSA

| Increased: | Decreased: |
|---|---|
| Uromodulin | Kallikrein 1 |
| Urocortin III | Zinc finger protein 81 |
| Bikunin | Zinc finger protein 36/1 |
| Tenascin | |
| Human Tribbles homologue 2 | |
| Orosomucoid 1 | |
| Alpha 1 microglobulin | |
| PCAF histone acetylase | |
| Prolyl hydroxylases domain | |

Based on the 2D-DIGE quantification approach using DECYDER™ software, 3 of these 12 proteins were significantly decreased in OSA, and the expression of the other 9 proteins was increased in OSA, as depicted in Table 4. There were no identifiable differences between PS and CO for these or other proteins.

Example 3

Immunoassay Analysis of Biomarkers in Obstructive Sleep Apnea

To confirm the identity of the candidate proteins that were differentially expressed in OSA urine samples, immunoblotting, enzyme-linked immunosorbent assay, or immunoturbidity approaches were utilized, mostly using commercially available antibodies.

First, immunoblotting was used to confirm the identity of Tenascin, Tribbles homologue 2, and Zinc finger protein 81 in the urine samples. Briefly, to perform the immunoblotting assays, urine sample proteins were first centrifuged for 10 minutes at 13,000 rpm. After centrifugation, soluble protein content was measured using a protein assay kit. Thirty μg of protein from each sample were then diluted 1:1 in SDS-polyacrylamide gel electrophoresis loading buffer and electrophoresed on 12% SDS-polyacrylamide gels (Invitrogen). Proteins were then transferred to ImmobilonP membranes (Millipore) and blocked for 2 hours at room temperature with blocking buffer (4% nonfat milk powder) in TBST (20 mmol/L Tris base; 500 mmol/L NaCl; 0.05% Tween 20, pH 7.4). Protein bands were immunolocalized on transblots with commercially-available primary antibodies followed by horseradish peroxidase-conjugated secondary anti-rabbit or anti-mouse antibody and developed by SuperSignal West Pico Chemiluminescent Substrate (Pierce). Quantification of protein bands was performed in triplicate for each sample by determination of the relative optical density (ImageJ).

Figure 2:
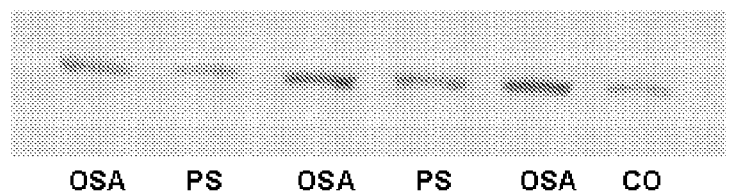
FIG. 2 includes images of western blots for Tenascin, Tribbles homologue 2, and Zinc finger protein 81 from children with OSA, from with children PS, and from healthy controls (CO).
Figure 2:
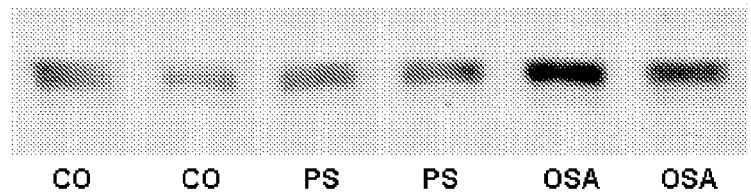
Figure 2:
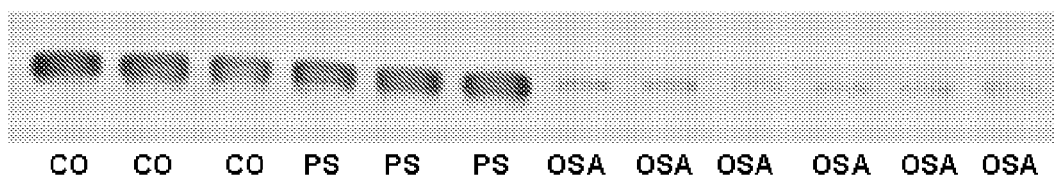

As shown in FIG. 2, the western blots confirmed the increased expression in urinary proteins of Tenascin and Tribbles homologue 2, and further confirmed the decreased expression of Zinc finger protein 81 in children with OSA, as compared to healthy controls and those with PS.

Urine levels of Kallikrein 1, Urocortin III, Uromodulin and Orosomucoid 1, were then confirmed and analyzed using ELISA assays or immunoturbidimetric assays. Briefly, urine levels for Kallikrein 1 and Uromodulin were assayed using commercially available ELISA kits following the manufacturer's instructions (Human Kallikrein/PSA DuoSet, cat #DY1344, R&D Systems, Minneapolis, Minn., which has a sensitivity of 0.03 ng/mL, exhibits linearity between 0.1-47.8 ng/ml, and has inter- and intra-assay coefficients of variability of 15.3.0% and 10.6%, respectively.; Human Uromodulin, MD Biosciences, cat #M036020, St Paul, Minn., which has a sensitivity of 6.62 ng/mL, exhibits linearity between 6.5-625 ng/ml, and has inter- and intra-assay coefficients of variability of 12.0% and 7.6%, respectively.). For Urocortin III, an in-house ELISA assay was developed using custom-made monoclonal antibodies raised against the c-terminal epitope of the published protein sequence. In preliminary assays, the sensitivity was 0.5 pg/ml, and linearity was exhibited from 0.7-35 pg/ml, with inter- and intra-assay coefficients of variability of 14.7 and 9.6%, respectively. Finally, urinary levels of Orosomucoid 1 were analyzed using a particle-enhanced immunoturbidimetric assay as previously reported (21). Urinary creatinine level was measured for each sample, and urine levels for the various peptides were corrected for corresponding urine creatinine concentration.

Once the levels of Kallikrein 1, Urocortin III, Uromodulin, and Orosomucoid 1 were determined in the urine samples, the sensitivity and specificity for each of the biomarkers were calculated on the basis of tabulating the number of correctly classified samples. Confidence intervals (95% CI) based on exact binomial calculations were carried out in MedCalc (version 8.1.1.0, MedCalc Software, Mariakerke, Belgium). A receiver operating characteristic (ROC) plot was then obtained by plotting all sensitivity values on the y axis against their equivalent 1-specificity values on the x axis for all available thresholds (MedCalc Software). Further, the area under the curve (AUC) was evaluated, as it provided a single measure of overall accuracy that was not dependent on a particular threshold (22). The reported unadjusted P-values were then calculated using the natural logarithm-transformed intensities and the Gaussian approximation to the t-distribution. Statistical adjustment for multiple testing was carried out by the method described by Reiner et al (23).

Figure 3A:
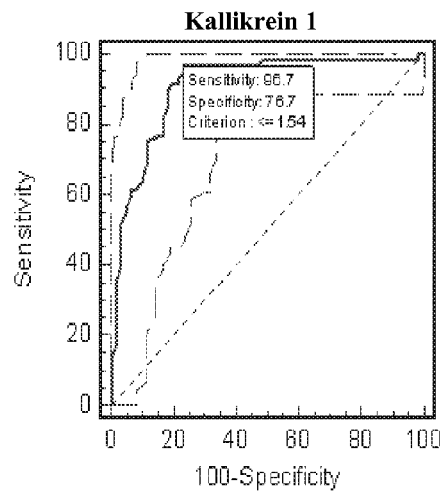
FIGS. 3A-3D include graphs showing receiver operator curves (ROC) for Kallikrein 1 (FIG. 3A), Urocortin III (FIG. 3B), Orosomucoid 1 (FIG. 3C), and Uromodulin (FIG. 3D) peptide levels, after correction for corresponding urinary creatinine concentrations.

Upon analysis of the results from these experiments, it was observed that Kallikrein 1 urine levels were significantly reduced in the urine samples of children with OSA. Indeed, Kallikrein 1 levels in CO children were 3.32±0.8 pg/ml/mg creatinine and were 3.02±0.6 pg/ml/mg creatinine in children with PS, but were 0.85±0.3 pg/ml/mg creatinine (p<0.001) in children diagnosed with OSA. Furthermore, ROC analyses revealed that Kallikrein 1 levels of ≤1.54 pg/ml/mg creatinine achieved 96.7% sensitivity and 76.7% specificity to predict OSA (FIG. 3A).

Figure 3B:
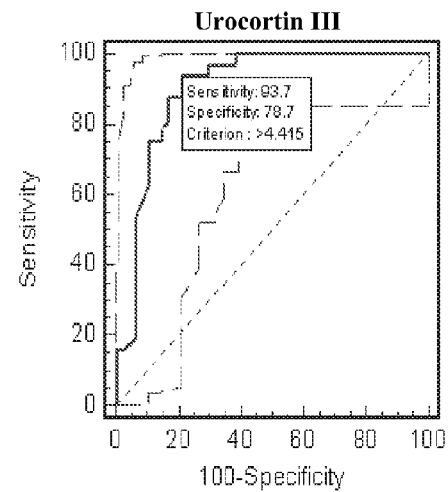

In contrast to the levels of Kallikrein 1 peptides that were detected in children with OSA, Urocortin III urine levels were significantly increased in OSA (6.9±0.4 pg/ml/mg creatinine) compared to either PS or CO (3.8±0.2 pg/ml/mg creatinine; p<0.001). Of note, custom developed ELISA assays for either Urocortin I or Urocortin II using commercially available antibodies showed similar levels for these proteins in the urine samples of the 3 groups, definitively confirming the high specificity of the 2D-DIGE-MS approach. Furthermore, ROC analyses revealed that Urocortin III levels of ≤4.4 pg/ml/mg creatinine achieved 93.7% sensitivity and 78.7% specificity to predict OSA (FIG. 3B).

Figure 3C:
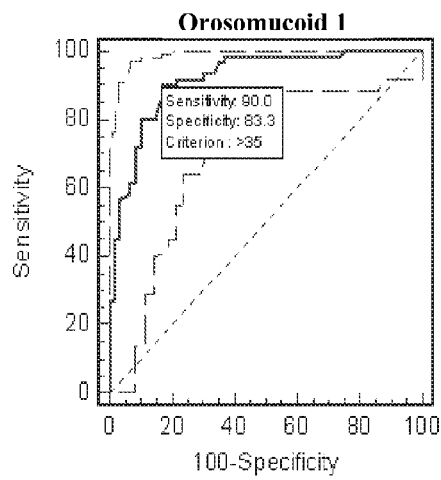
Figure 3D:
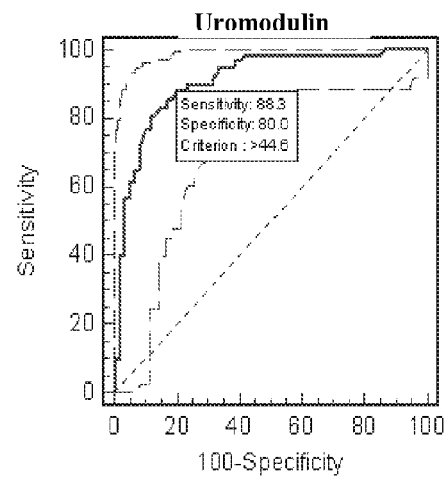

Uromodulin peptide levels were also increased in OSA (156.4±13.0 ng/ml/mg creatinine compared to 29.1±6.9 ng/ml/mg creatinine in CO (p<0.0001), and 37.8±10.6 ng/ml/mg creatinine in PS (p<0.0001 vs. OSA). Additionally, ROC analyses revealed that Uromodulin levels of >44.6 pg/ml/mg creatinine achieved 88.3% sensitivity and 80.0% specificity to predict OSA (FIG. 3D).

Figure 4:
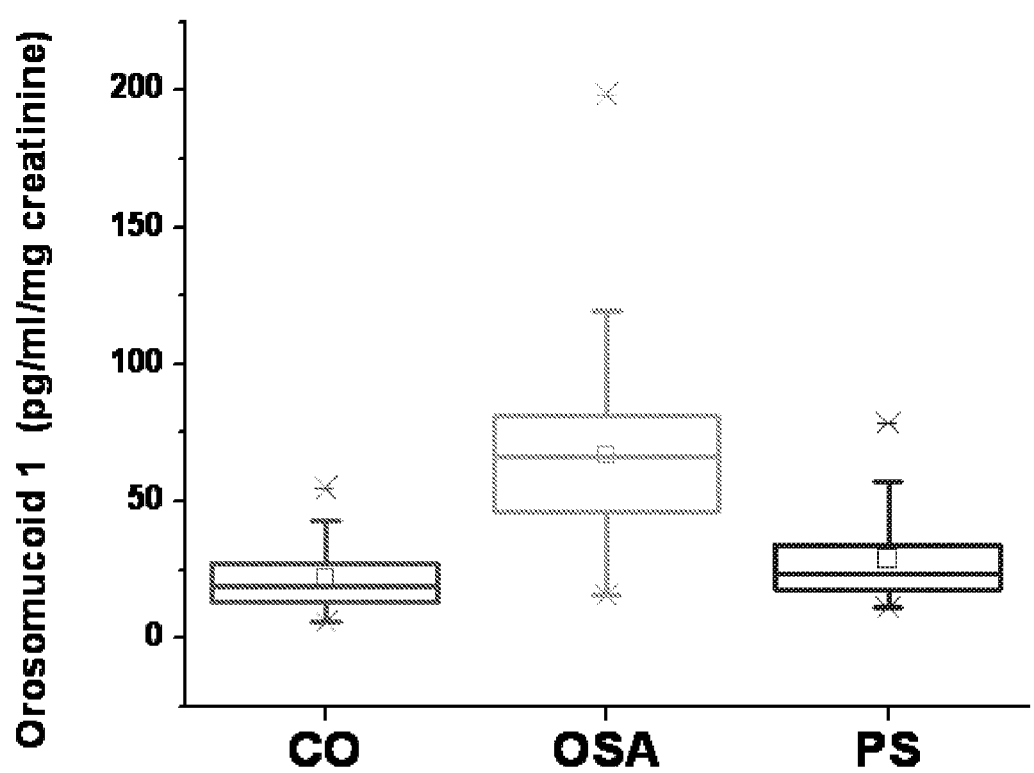
FIG. 4 is a graph showing boxplots of urinary concentrations of Orosomucoid 1, after correction for corresponding urinary creatinine concentrations, in 30 control children (CO), 30 children with primary snoring (PS), and 60 children with obstructive sleep apnea (OSA).

Orosomucoid 1 levels were measured in all urine samples. PS and CO Orosomucoid 1 urine levels were similar and were therefore merged. Their mean values were 25.0±1.8 pg/ml/mg creatinine compared to 67.1±3.9 pg/ml/mg creatinine in individuals diagnosed with OSA (p<0.0001; FIG. 4). In that regard, ROC analyses further revealed that Orosomucoid 1 levels of >35 pg/ml/mg creatinine achieved 90% sensitivity and 83.3% specificity to predict OSA (FIG. 3C).

Figure 5:
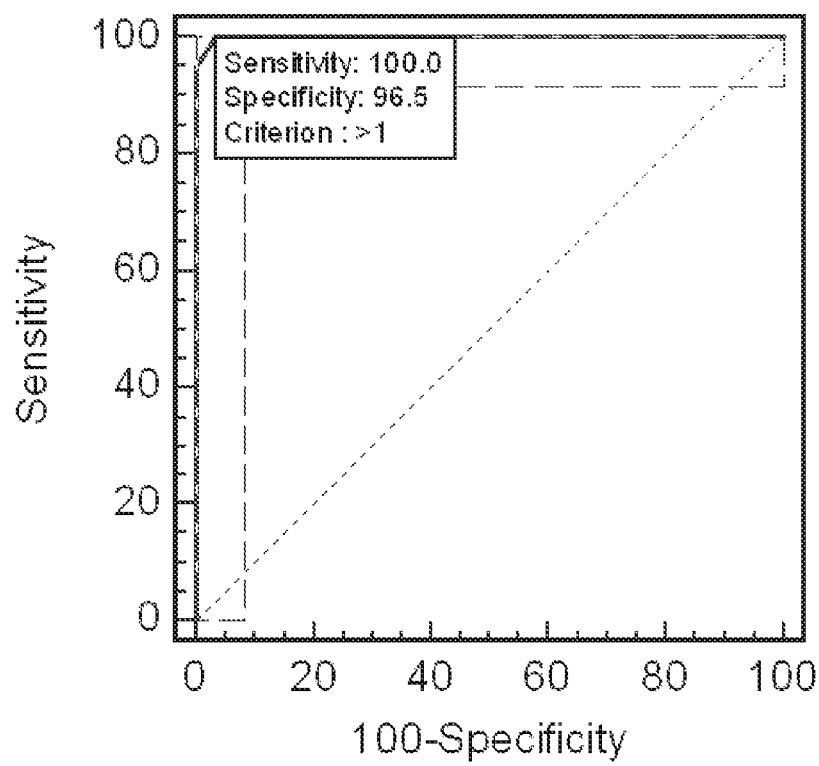
FIG. 5 is a graph showing receiver operator curves for combinatorial analyses using one or more cut-off levels defined for Kallikrein 1, Urocortin III, and Orosomucoid 1, and Uromodulin urine levels, after correction for corresponding urinary creatinine concentrations.
Figure 6:
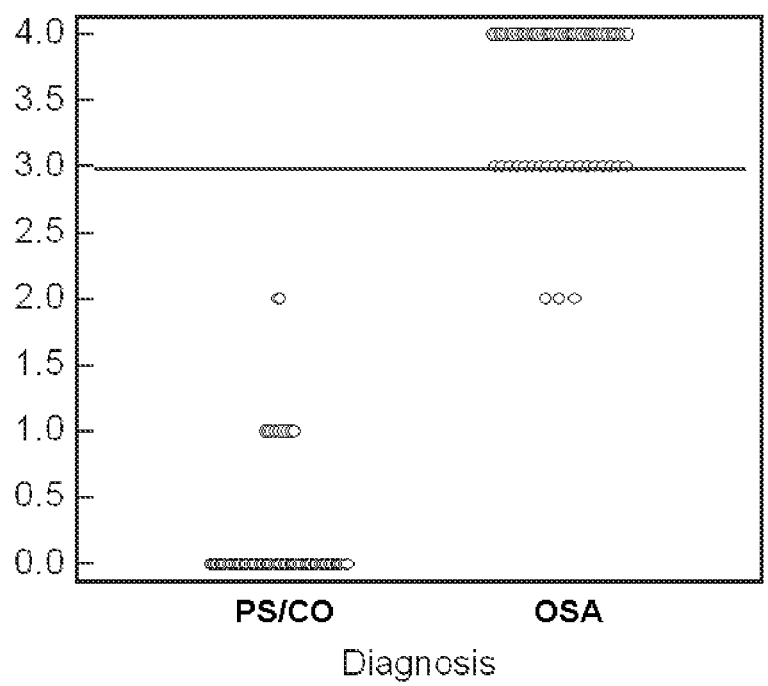
FIG. 6 is a dot plot illustrating the discriminatory ability of using 3 or more cut off levels defined for Kallikrein 1, Urocortin III, Orosomucoid 1, and Uromodulin urine levels, after correction for corresponding urinary creatinine concentrations.

The ROC analyses described above revealed that the Kallikrein 1, Urocortin III, Uromodulin and Orosomucoid 1 peptides could be used independently as reliable markers for OSA. However, ROC analyses using those 4 peptides in combination revealed that if all 4 peptide biomarkers were employed, the presence of levels exceeding the cut-offs described above for two or more of the proteins yielded a 100% sensitivity and 96.5% specificity to predict OSA (FIG. 5). Moreover, the presence of levels exceeding the cut-offs described above for 3 or more of the 4 peptides yielded a 95% sensitivity and 100% specificity to diagnose OSA (FIG. 6).

For those 4 proteins for which quantitative assessments were possible for the whole cohort, namely Kallikrein 1, Urocortin III, Uromodulin, and Orosomucoid 1, ROC analyses for each of the proteins were globally sensitive and specific in identification of OSA, and, furthermore, combinatorial approaches yielded highly predictive performances. Taken together these results thus indicate that a determination of the amounts of Kallikrein 1, Urocortin III, Uromodulin, and Orosomucoid 1 peptides, either alone or in combination, in a biological sample can be used as an effective diagnostic tool for OSA.

Throughout this document, various references are mentioned. All such references are incorporated herein by reference, including the references set forth in the following list:

References

1. Sans Capdevila O, Kheirandish-Gozal L, Dayyat E, Gozal D. Pediatric obstructive sleep apnea: Complications, management, and long-term outcomes. Proc Am Thor Soc 2008; 5:274-282.

2. Gozal D. Obstructive sleep apnea in children: implications for the developing central nervous system. Semin Pediatr Neurol. 2008 June; 15(2):100-6.
3. Gozal D, Kheirandish-Gozal L. Cardiovascular morbidity in obstructive sleep apnea: oxidative stress, inflammation, and much more. Am J Respir Crit Care Med. 2008 Feb. 15; 177(4):369-75.
4. O'Brien L M, Mervis C B, Holbrook C R, Bruner J L, Smith N H, McNally N, McClimment M C, Gozal D. Neurobehavioral correlates of sleep-disordered breathing in children. J Sleep Res. 2004 June; 13(2):165-72.
5. Ferreira A M, Clemente V, Gozal D, Gomes A, Pissarra C, César H, Coelho I, Silva C F, Azevedo M H P. Snoring in Portuguese primary school children. Pediatrics 2000; 106 (5).
6. O'Brien L M, Holbrook C R, Mervis C B, Klaus C J, Bruner J, Raffield T J, Rutherford J, Mehl R C, Wang M, Tuell A, Hume B C, Gozal D. Sleep and neurobehavioral characteristics in 5-7-year-old hyperactive children. Pediatrics 2003; 111:554-563.
7. Urschitz M S, Guenther A, Eitner S, Urschitz-Duprat P M, Schlaud M, Ipsiroglu O S, Poets C F. Risk factors and natural history of habitual snoring. Chest. 2004; 126:790-800.
8. Kaditis A G, Finder J, Alexopoulos E I, Starantzis K, Tanou K, Gampeta S, Agorogiannis E, Christodoulou S, Pantazidou A, Gourgoulianis K, Molyvdas P A. Sleep-disordered breathing in 3,680 Greek children. Pediatr Pulmonol. 2004; 37:499-509.
9. Rosen C L, Larkin E K, Kirchner H L, Emancipator J L, Bivins S F, Surovec S A, Martin R J, Redline S. Prevalence and risk factors for sleep-disordered breathing in 8- to 11-year-old children: association with race and prematurity. J. Pediatr. 2003; 142:383-389.
10. Montgomery-Downs H E, O'Brien L M, Holbrook C R, Gozal D. Snoring and sleep-disordered breathing in young children: Subjective and objective correlates. Sleep 2004; 27:87-94.
11. Montgomery-Downs H E, Gozal D. Sleep habits and risk factors for sleep-disordered breathing in infants and young toddlers in Louisville, Ky. Sleep Med 2006; 7:211-219.
12. Carroll J L, McColley S A, Marcus C L, Curtis S, Loughlin G M. Inability of clinical history to distinguish primary snoring from obstructive sleep apnea syndrome in children. Chest. 1995; 108(3):610-618.
13. Wang R C, Elkins T P, Keech D, Wauquier A, Hubbard D. Accuracy of clinical evaluation in pediatric obstructive sleep apnea. Otolaryngol Head Neck Surg. 1998; 118(1): 69-73.
14. Bhattacharjee R, Dayyat E, Kheirandish-Gozal L, Capdevila O S, Gozal D. Nocturnal polysomnographic characteristics of habitually snoring children initially referred to pediatric ENT or sleep clinics. Sleep Med. 2009 May 16.
15. Obstructive Sleep Apnea Syndrome. Technical report: diagnosis and management of childhood obstructive sleep apnea syndrome. Pediatrics. 2002; 109(4):e69.
16. Krishna J, Shah Z A, Merchant M, Klein J B, Gozal D. Urinary protein expression patterns in children with sleep-disordered breathing: preliminary findings. Sleep Med. 2006; 7(3):221-227.
17. Larbi N B, Jefferies C. 2D-DIGE: Comparative proteomics of cellular signaling pathways. Methods Mol Biol. 2009; 517:1-28.
18. Montgomery-Downs H E, O'Brien L M, Gulliver T E, Gozal D. Polysomnographic characteristics in normal preschool and early school-aged children. Pediatrics 2006; 117(3):741-753.
19. Rechstschaffen A, Kales A. A Manual of Standardized Terminology, Techniques and Scoring System for Sleep Stages of Human Subjects. Brain Information Services/Brain Research Institute, University of California, Los Angeles 1968.
20. EEG arousals: scoring rules and examples: a preliminary report from the Sleep Disorders Atlas Task Force of the American Sleep Disorders Association. Sleep 1992; 15(2): 173-84.
21. Christiansen, M. S., Blirup-Jensen, S., Foged, L., Larsen, M. and Magid, E. A particle-enhanced turbidimetric immunoassay for quantitative determination of orosomucoid in urine: development, validation and reference values. Clin Chem Lab Med 2004; 42:1168-1177.
22. DeLeo J. Receiver operating characteristic laboratory (ROCLAB): software for developing decision strategies that account for uncertainty. In: Ayyub B M (ed). *Proceedings Second International Symposium on Uncertainty Modeling and Analysis* (College Park, Md., USA). IEEE Computer Society Press, 1993, pp 318-325.
23. Reiner A, Yekutieli D, Benjamini Y. Identifying differentially expressed genes using false discovery rate controlling procedures. Bioinformatics 2003; 19: 368-375.
24. Zolotarjova N, Martosella J, Nicol G, Bailey J, Boyes B E, Barrett W C. Differences among techniques for high-abundant protein depletion. Proteomics 2005; 5:3304-13.
25. Liu H, Sadygov R G, Yates J R 3rd. A model for random sampling and estimation of relative protein abundance in shotgun proteomics. Anal Chem 2004; 76:4193-201.
26. Old W M, Meyer-Arendt K, Aveline-Wolf L, Pierce K G, Mendoza A, Sevinsky J R, Resing K A, Ahn N G. Comparison of label-free methods for quantifying human proteins by shotgun proteomics. Mol Cell Proteomics 2005; 4:1487-502.
27. Nesvizhskii A I, Vitek O, Aebersold R. Analysis and validation of proteomic data generated by tandem mass spectrometry. Nat Methods 2007; 4:787-97.
28. Pisitkun T, Shen R F, Knepper M A. Identification and proteomic profiling of exosomes in human urine. Proc Natl Acad Sci USA 2004; 101:13368-13373.
29. Fukuoka S, Kobayashi K. Analysis of the C-terminal structure of urinary Tamm-Horsfall protein reveals that the release of the glycosyl phosphatidylinositol-anchored counterpart from the kidney occurs by phenylalanine-specific proteolysis. Biochem Biophys Res Commun 2001; 289: 1044-1048.
30. El-Achkar T M, Wu X R, Rauchman M, McCracken R, Kiefer S, Dagher P C. Tamm-Horsfall protein protects the kidney from ischemic injury by decreasing inflammation and altering TLR4 expression. Am J Physiol Renal Physiol. 2008; 295(2):F534-F544.
31. Serafini-Cessi F, Malagolini N, Cavallone D. Tamm-Horsfall glycoprotein: biology and clinical relevance. Am J Kidney Dis 2003; 42: 658-676.
32. Thornley C, Dawnay A, Cattell W R. Human Tamm-Horsfall glycoprotein: urinary and plasma levels in normal subjects and patients with renal disease determined by a fully validated radioimmunoassay. Clin Sci (Lond) 1985; 68: 529-535.
33. Lynn K L, Marshall R D. Excretion of Tamm-Horsfall glycoprotein in renal disease. Clin Nephrol 1984; 22: 253-257.
34. Pugia M J, Valdes R Jr, Jortani S A. Bikunin (urinary trypsin inhibitor): structure, biological relevance, and measurement. Adv Clin Chem. 2007; 44:223-45.
35. Pugia M J, Jortani S A, Basu M, Sommer R, Kuo H H, Murphy S, Williamson D, Vranish J, Boyle P J, Budzinski D, Valdes R Jr, Basu S C. Immunological evaluation of urinary trypsin inhibitors in blood and urine: role of N- & O-linked glycoproteins. Glycoconj J. 2007; 24(1):5-15.0.
36. Penders J, Delanghe J R. Alpha 1-microglobulin: clinical laboratory aspects and applications. Clin Chim Acta. 2004; 346(2):107-118.
37. Guder W G, Hofmann W. Clinical role of urinary low molecular weight proteins: their diagnostic and prognostic implications. Scand J Clin Lab Invest Suppl. 2008; 241: 95-98.
38. Khalyfa A, Capdevila O S, Buazza M O, Serpero L D, Kheirandish-Gozal L, Gozal D. Genome-wide gene expression profiling in children with non-obese obstructive sleep apnea. Sleep Med. 2009; 10(1):75-86.
39. Bhattacharjee R, Kheirandish-Gozal L, Pillar G, Gozal D. Cardiovascular complications of obstructive sleep apnea syndrome: evidence from children. Prog Cardiovasc Dis. 2009; 51(5):416-433.
40. Deng J, James C H, Patel L, Smith A, Burnand K G, Rahmoune H, Lamb J R, Davis B. Human tribbles homologue 2 is expressed in unstable regions of carotid plaques and regulates macrophage IL-10 in vitro. Clin Sci (Lond). 2009; 116(3):241-248.
41. Gozal D, Capdevila O S, Kheirandish-Gozal L. Metabolic alterations and systemic inflammation in obstructive sleep apnea among nonobese and obese prepubertal children. Am J Respir Crit Care Med. 2008; 177(10):1142-1149.
42. Gozal D, Serpero L D, Sans Capdevila O, Kheirandish-Gozal L. Systemic inflammation in non-obese children with obstructive sleep apnea. Sleep Med. 2008; 9(3):254-259.
43. Gozal D, Kheirandish-Gozal L, Serpero L D, Sans Capdevila O, Dayyat E. Obstructive sleep apnea and endothelial function in school-aged nonobese children: effect of adenotonsillectomy. Circulation. 2007; 116(20):2307-2314.
44. Naiki T, Saijou E, Miyaoka Y, Sekine K, Miyajima A. TRB2, a mouse Tribbles ortholog, suppresses adipocyte differentiation by inhibiting AKT and C/EBPbeta. J Biol Chem. 2007; 282(33):24075-24082.
45. Fournier T, Medjoubi-N N, Porquet D. Alpha-1-acid glycoprotein. Biochim Biophys Acta. 2000; 1482(1-2):157-171.
46. Schmid K, Nimerg R B, Kimura A, Yamaguchi H, Binette J P. The carbohydrate units of human plasma α1-acid glycoprotein. Biochim. Biophys. Acta 1977; 492:291-302.
47. Mackiewicz A, Ganapathi M K, Schultz D, Kushner I. Monokines regulate glycosylation of acute-phase proteins. J. Exp. Med. 1987; 166:253-258.
48. de Graaf T W, van der Stelt M E, Anbergen M G, van Dijk W. Inflammation-induced expression of sialyl LewisX-containing glycan structures on α1-acid glycoprotein (orosomucoid) in human sera. J. Exp. Med. 1993; 177:657-666.
49. Costello M J, Gewurz H, Siegel J N Inhibition of neutrophil activation by α1-acid glycoprotein. Clin. Exp. Immunol. 1984: 55:465-472.
50. Andersen P, Godal H C. The antiheparin effect of α1-acid glycoprotein probably due to steric hindrance of the heparin-thrombin interaction. Thromb. Res. 1979; 15:857-868.
51. Boncela J, Papiewska I, Fijalkowska I, Walkowiak B, Cierniewski C S. Acute phase protein α1-acid glycoprotein interacts with plasminogen activator inhibitor type 1 and stabilizes its inhibitory activity. J. Biol. Chem. 2001; 276: 35305-35311.
52. Sörensson J, Matejka G L, Ohlson M, Haraldsson B. Human endothelial cells produce orosomucoid, an important component of the capillary barrier. Am. J. Physiol. 1999; 276:H530-534.
53. Benedek I H, Blouin R A, McNamara P J. Serum protein binding and the role of increased alpha 1-acid glycoprotein in moderately obese male subjects. Br J Clin Pharmacol 1984; 18: 941-946.
54. Raynaud-Simon A, Lafont S, Berr C, Dartigues J F, Le Bouc Y. Orosomucoid: a mortality risk factor in elderly people living in the community? Clin Nutr. 2002; 21(1): 45-50.
55. Maachi M, Piéroni L, Bruckert E, Jardel C, Fellahi S, Hainque B, Capeau J, Bastard J P. Systemic low-grade inflammation is related to both circulating and adipose tissue TNFalpha, leptin and IL-6 levels in obese women. Int J Obes Relat Metab Disord. 2004; 28(8):993-997.
56. Christiansen M S, Iversen K, Larsen C T, Goetze J P, Hommel E, Mølvig J, Pedersen B K, Magid E, Feldt-Rasmussen B. Increased urinary orosomucoid excretion: a proposed marker for inflammation and endothelial dysfunction in patients with type 2 diabetes. Scand J Clin Lab Invest. 2009; 69(2):272-281.
57. Jiang H, Guan G, Zhang R, Liu G, Liu H, Hou X, Cheng J. Increased urinary excretion of orosomucoid is a risk predictor of diabetic nephropathy. Nephrology (Carlton). 2009 Jan. 8.
58. Vassilev A, Yamauchi J, Kotani T, Prives C, Avantaggiati M L, Qin J, Nakatani Y. The 400 kDa subunit of the PCAF histone acetylase complex belongs to the ATM superfamily. Mol Cell. 1998; 2(6):869-875.
59. Ginouvès A, Ilc K, Macías N, Pouysségur J, Berra E. PHDs overactivation during chronic hypoxia "desensitizes" HIFalpha and protects cells from necrosis. Proc Natl Acad Sci USA. 2008; 105(12):4745-4750.
60. Chen C F, Chen L W, Chien C T, Wu M S, Tsai T J. Renal kallikrein in chronic hypoxic rats. Clin Exp Pharmacol Physiol. 1996; 23(9):819-824.
61. Thongboonkerd V, Gozal E, Sachleben L R Jr, Arthur J M, Pierce W M, Cai J, Chao J, Bader M, Pesquero J B, Gozal D, Klein J B. Proteomic analysis reveals alterations in the renal kallikrein pathway during hypoxia-induced hypertension. J Biol Chem. 2002; 277(38):34708-34716.
62. Amin R, Somers V K, McConnell K, Willging P, Myer C, Sherman M, McPhail G, Morgenthal A, Fenchel M, Bean J, Kimball T, Daniels S. Activity-adjusted 24-hour ambulatory blood pressure and cardiac remodeling in children with sleep disordered breathing. Hypertension. 2008; 51(1):84-91.
63. Bell S E, Sanchez M J, Spasic-Boskovic O, Santalucia T, Gambardella L, Burton G J, Murphy J J, Norton J D, Clark A R, Turner M. The RNA binding protein Zfp36l1 is required for normal vascularisation and post-transcriptionally regulates VEGF expression. Dev Dyn. 2006; 235(11): 3144-3155.
64. Kwon H S, Shin H C, Kim J S. Suppression of vascular endothelial growth factor expression at the transcriptional and post-transcriptional levels. Nucleic Acids Res. 2005; 33(8):e74.
65. Gozal D, Lipton A J, Jones K L. Circulating vascular endothelial growth factor levels in patients with obstructive sleep apnea. Sleep. 2002; 25(1):59-65.
66. Lavie L, Kraiczi H, Hefetz A, Ghandour H, Perelman A, Hedner J, Lavie P. Plasma vascular endothelial growth factor in sleep apnea syndrome: effects of nasal continuous positive air pressure treatment. Am J Respir Crit Care Med. 2002; 165(12):1624-1628.

67. Slominski A, Roloff B, Curry J, Dahiya M, Szczesniewski A, Wortsman J. The skin produces urocortin. *Journal of Clinical Endocrinology & Metabolism.* 2000 February; 85(2): 815-23.
68. U.S. Pat. No. 6,989,100 to Norton, issued Jan. 24, 2006, entitled "Methods for time-alignment of liquid chromatography-mass spectrometry data."
69. U.S. Pat. No. 6,925,389 to Hitt, et al., issued Aug. 2, 2005, entitled "Process for discriminating between biological states based on hidden patterns from biological data."
70. U.S. Pat. No. 6,890,763 to Jackowski, et al., issued May 10, 2005, entitled "Biopolymer marker indicative of disease state having a molecular weight of 1350 daltons."
71. U.S. Pat. No. 6,143,576 to Buechler, issued Nov. 7, 2000, entitled "Non-porous diagnostic devices for the controlled movement of reagents."
72. U.S. Pat. No. 6,113,855 to Buechler, issued Sep. 5, 2000, entitled "Devices comprising multiple capillarity inducing surfaces."
73. U.S. Pat. No. 6,019,944 to Buechler, issued Feb. 1, 2000, entitled "Diagnostic devices and apparatus for the controlled movement of reagents without membranes."
74. U.S. Pat. No. 5,985,579 to Buechler, et al., issued Nov. 16, 1999, entitled "Antibodies to complexes of ligand receptors and ligands and their utility in ligand-receptor assays."
75. U.S. Pat. No. 5,955,377 to Maul, et al., issued Sep. 21, 1999, entitled "Methods and kits for the amplification of thin film based assays."
76. U.S. Pat. No. 5,947,124 to Buechler, et al., issued Sep. 7, 1999, entitled "Diagnostic for determining the time of a heart attack."
77. U.S. Pat. No. 5,939,272 to Buechler, et al., issued Aug. 17, 1999, entitled "Non-competitive threshold ligand-receptor assays."
78. U.S. Pat. No. 5,922,615 to Nowakowski, et al., issued Jul. 13, 1999, entitled "Assay devices comprising a porous capture membrane in fluid-withdrawing contact with a nonabsorbent capillary network."
79. U.S. Pat. No. 5,885,527 to Buechler, issued Mar. 23, 1999, entitled "Diagnostic devices and apparatus for the controlled movement of reagents without membranes."
80. U.S. Pat. No. 5,851,776 to Valkirs, issued Dec. 22, 1998, entitled "Conjugates and assays for simultaneous detection of multiple ligands."
81. U.S. Pat. No. 5,824,799 to Buechler, et al., issued Oct. 20, 1998, entitled "Hybrid phthalocyanine derivatives and their uses."
82. U.S. Pat. No. 5,679,526 to Buechler, et al., issued Oct. 21, 1997, entitled "Threshold ligand-receptor assay."
83. U.S. Pat. No. 5,631,171 to Sandstrom, et al., issued May 20, 1997, entitled "Method and instrument for detection of change of thickness or refractive index for a thin film substrate."
84. U.S. Pat. No. 5,525,524 to Buechler, et al., issued Jun. 11, 1996, entitled "Crosstalk inhibitors and their uses."
85. U.S. Pat. No. 5,480,792 to Buechler, et al., issued Jan. 2, 1996, entitled "Antibodies to complexes of ligand receptors and ligands and their utility in ligand-receptor assays."
86. Culture Of Animal Cells, R. I. Freshney, Alan R. Liss, Inc., 1987.
87. DNA Cloning, Volumes I and II, Glover, ed., 1985.
88. Gene Transfer Vectors For Mammalian Cells, J. H. Miller and M. P. Calos, eds., Cold Spring Harbor Laboratory, 1987.
89. Handbook Of Experimental Immunology, Volumes I-IV, D. M. Weir and C. C. Blackwell, eds., 1986.
90. Immobilized Cells And Enzymes, IRL Press, 1986.
91. Immunochemical Methods In Cell And Molecular Biology (Mayer and Walker, eds., Academic Press, London, 1987.
92. Methods In Enzymology, Vols. 154 and 155, Wu et al., eds., Academic Press Inc., N.Y.
93. Molecular Cloning A Laboratory Manual (1989), 2nd Ed., ed. by Sambrook, Fritsch and Maniatis, eds., Cold Spring Harbor Laboratory Press, Chapters 16 and 17.
94. Nucleic Acid Hybridization, D. Hames & S. J. Higgins, eds., 1984.
95. Oligonucleotide Synthesis, M. J. Gait, ed., 1984.
96. Perbal (1984), A Practical Guide To Molecular Cloning; See Methods In Enzymology (Academic Press, Inc., N.Y.).
97. Transcription and Translation, B. D. Hames & S. J. Higgins, eds., 1984.

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. A method for diagnosing obstructive sleep apnea in a subject, comprising:
    (a) providing a biological sample from the subject;
    (b) determining an amount in the sample of a Urocortin III peptide;
    (c) determining an amount in the sample of a Uromodulin peptide, an Orosomucoid 1 peptide, a Kallikrein 1 peptide, or a combination thereof;
    (d) comparing the amount of the Urocortin III peptide in the sample, if present, to a control level of the Urocortin III peptide,
    (e) comparing the amount of the Uromodulin peptide, the Orosomucoid 1 peptide, the Kallikrein 1 peptide, or the combination thereof in the sample, if present, to a control level of the Uromodulin peptide, the Orosomucoid 1 peptide, the Kallikrein 1 peptide, or the combination thereof; and
    (f) diagnosing the subject as having obstructive sleep apnea, or a risk thereof, if there is a measurable increase in the amount of the Urocortin III peptide and if there is a measurable increase in the amount of the Uromodulin peptide, a measurable increase in the amount of the Orosomucoid 1 peptide, a measurable decrease in the amount of the Kallikrein 1 peptide, or the combination thereof in the sample as compared to the control levels,
    wherein determining the amount in the sample of the Urocortin III peptide and the amount in the sample of the Uromodulin peptide, the Orosomucoid 1 peptide, the Kallikrein 1 peptide, or the combination thereof comprises determining the amount in the sample using mass spectrometry (MS) analysis, immunoassay analysis, or both,
    wherein the mass spectrometry (MS) analysis is selected from the group consisting of liquid-chromatography mass spectrometry (LC-MS), electrospray ionization mass spectrometry (ESI-MS), matrix-assisted laser desorption ionization time-of-flight mass spectrometry (MALDI-TOF-MS), and surface-enhanced laser desorption/ionization time-of-flight mass spectrometry (SELDI-TOF-MS), and
    wherein the immunoassay analysis is selected from the group consisting of an enzyme-linked immunosorbent assay (ELISA) and an immunoturbidimetric assay.

2. The method of claim 1, wherein the biological sample comprises urine, saliva, blood, plasma, or serum.

3. The method of claim 1, wherein the subject is human.

4. The method of claim 3, wherein the subject is human and under the age of about 9 to about 2 years of age.

5. The method of claim 1, wherein the step of determining an amount in the sample of a Uromodulin peptide, an Orosomucoid 1 peptide, a Kallikrein 1 peptide, or a combination thereof comprises determining an amount in the sample of a Uromodulin peptide, an Orosomucoid 1 peptide, and a Kallikrein 1 peptide.

6. The method of claim 1, further comprising selecting a treatment or modifying a treatment for the obstructive sleep apnea based on the determined amount of the Urocortin III peptide.

7. A method for determining whether to initiate or continue prophylaxis or treatment of obstructive sleep apnea in a subject, comprising:
  (a) providing a series of biological samples over a time period from the subject;
  (b) analyzing the series of biological samples to determine an amount in each of the biological samples of a Urocortin III peptide;
  (c) analyzing the series of biological samples to determine an amount in each of the biological samples of a Uromodulin peptide, an Orosomucoid 1 peptide, a Kallikrein 1 peptide, or a combination thereof;
  (d) comparing any measurable change in the amounts of the Urocortin III peptide in each of the biological samples;
  (e) comparing any measurable change in the amounts of the Uromodulin peptide, the Orosomucoid 1 peptide, the Kallikrein 1 peptide, or the combination thereof in each of the biological samples; and
  (f) determining whether to initiate or continue the prophylaxis or therapy of the obstructive sleep apnea based on any measurable changes in the amounts of the Urocortin III peptide in each of the biological samples and any measurable changes in the amounts of the Uromodulin peptide, the Orosomucoid 1 peptide, the Kallikrein 1 peptide, or the combination thereof in each of the biological samples,
  wherein analyzing the series of biological samples to determine the amount in each of the biological samples of the Urocortin III peptide and the amount in each of the biological samples of the Uromodulin peptide, the Orosomucoid 1 peptide, the Kallikrein 1 peptide, or the combination thereof comprises determining the amount in the sample using mass spectrometry analysis, immunoassay analysis, or both,
  wherein the mass spectrometry (MS) analysis is selected from the group consisting of liquid-chromatography mass spectrometry (LC-MS), electrospray ionization mass spectrometry (ESI-MS), matrix-assisted laser desorption ionization time-of-flight mass spectrometry (MALDI-TOF-MS), and surface-enhanced laser desorption/ionization time-of-flight mass spectrometry (SELDI-TOF-MS), and
  wherein the immunoassay analysis is selected from the group consisting of an enzyme-linked immunosorbent assay (ELISA) and an immunoturbidimetric assay.

8. The method of claim 7, wherein the biological sample comprises urine, saliva, blood, plasma, or serum.

9. The method of claim 7, wherein the subject is human.

10. The method of claim 9, wherein the subject is human and under the age of about 9 to about 2 years of age.

11. The method of claim 7, wherein the series of biological samples comprises a first biological sample collected prior to initiation of the prophylaxis or treatment for the obstructive sleep apnea and a second biological sample collected after initiation of the prophylaxis or treatment.

12. The method of claim 7, wherein the step of analyzing the series of biological samples to determine an amount in each of the biological samples of a Uromodulin peptide, an Orosomucoid 1 peptide, a Kallikrein 1 peptide, or a combination thereof comprises analyzing the series of biological samples to determine an amount in each of the biological samples of a Uromodulin peptide, an Orosomucoid 1 peptide, and a Kallikrein 1 peptide.

13. The method of claim 1, further comprising modifying or prescribing a suitable treatment if the subject is diagnosed as having or at an increased risk of developing obstructive sleep apnea.

* * * * *